(12) United States Patent
Beatch et al.

(10) Patent No.: US 6,979,685 B1
(45) Date of Patent: Dec. 27, 2005

(54) CYCLOALKYL AMINE COMPOUNDS AND USES THEREOF

(75) Inventors: Gregory N. Beatch, Vancouver (CA); Bertrand M. C. Plouvier, Vancouver (CA); Michael J. A. Walker, Vancouver (CA); Richard A. Wall, Vancouver (CA); Alexander B. Zolotoy, Richmond (CA)

(73) Assignee: Cardiome Pharma Corp., Vancouver (CA)

( * ) Notice: Subject to any disclaimer, the term of this patent is extended or adjusted under 35 U.S.C. 154(b) by 0 days.

(21) Appl. No.: 09/913,373

(22) PCT Filed: Feb. 10, 2000

(86) PCT No.: PCT/CA00/00117

§ 371 (c)(1),
(2), (4) Date: Jan. 28, 2002

(87) PCT Pub. No.: WO00/47547

PCT Pub. Date: Aug. 17, 2000

Related U.S. Application Data

(60) Provisional application No. 60/119,887, filed on Feb. 12, 1999.

(51) Int. Cl.[7] .................. A61K 31/535; A61K 31/40; C07D 413/60; C07D 207/12
(52) U.S. Cl. .................. 514/231.2; 514/424; 544/140; 548/544
(58) Field of Search .................. 514/239.2, 424; 544/174; 548/541

(56) References Cited

U.S. PATENT DOCUMENTS

| | | | |
|---|---|---|---|
| 4,145,435 A | 3/1979 | Szmuszkovicz | 424/274 |
| 4,880,800 A | 11/1989 | Wallis et al. | 514/211 |
| 5,637,583 A * | 6/1997 | MacLeod et al. | |
| 6,451,819 B2 * | 9/2002 | Alanine et al. | 514/326 |
| 6,521,619 B2 * | 2/2003 | Link et al. | 514/237.2 |
| 6,649,603 B2 * | 11/2003 | Sum | 514/210.01 |

FOREIGN PATENT DOCUMENTS

| | | |
|---|---|---|
| DE | 2 259 260 | 6/1974 |
| DE | 3 517 901 | 12/1985 |
| JP | 02-270864 | 11/1990 |
| WO | WO 94/14435 | 7/1994 |
| WO | WO 96/23894 | 8/1996 |

OTHER PUBLICATIONS

Crotti et al., "Regiochemical Control of the Ring-Opening of Epoxides by Means of Chelating Processes. Part 13. Synthesis and Ring-Opening Reactions of the Diastereoisomeric cis- and Transepoxides Derived From 3-(benzyloxy)cyclopentene and 2-(benzyloxy)-2, 5-dihydrofuran, " *Chemical Abstracts 129*(17):662-663, abstract No. 216472k, Oct. 26, 1998.

Morisawa et al., "Preparation of Flourocarbocyclic Nucleosides as Antitumor Agents," *Chemical Abstracts 115* (5):904-905, abstract No. 50215n, Aug. 5, 1991.

Orth et al., "Cyclopentane-1-amines," *Chemical Abstracts 89*(15):555, abstract No. 129113f, Oct. 9, 1978.

Abstract of DE 2 259 260, Derwent World Patents Index, Jun. 6, 1974.

Abstracts of JP 02-270864, espacenet database, Nov. 5, 1990.

* cited by examiner

*Primary Examiner*—Deborah C. Lambkin
(74) *Attorney, Agent, or Firm*—Seed IP Law Group PLLC

(57) ABSTRACT

Aminocycloalkyl compounds are disclosed. The compounds of the present invention may be incorporated in compositions and kits. The present invention also discloses a variety of in vitro and in vivo uses for the compounds and compositions, including the treatment of arrhythmia and the production of local analgesia and anesthesia.

88 Claims, 4 Drawing Sheets

CYCLOALKYL AMINE COMPOUNDS AND USES THEREOF

This application is a 371 of PCT/CA00/00117 filed on Feb. 10, 2000 which claims the benefit of Provisional application Ser. No. 60/119,887 filed Feb. 12, 1999.

TECHNICAL FIELD

The present invention is generally directed toward cycloalkyl amine compounds such as aminocycloalkyl ether compounds and aminocycloalkyl ester compounds, pharmaceutical compositions and kits containing the cycloalkyl amine compounds, and therapeutic uses thereof.

BACKGROUND OF THE INVENTION

Arrhythmia is a variation from the normal rhythm of the heart beat. The major cause of fatalities due to cardiac arrhythmias is the subtype of arrhythmias known as ventricular fibrillation. Conservative estimates indicate that, in the U.S. alone, approximately 300,000 individuals per year suffer heart attacks. Approximately half of these die from sudden cardiac death, the major cause of which is ventricular fibrillation.

Antiarrhythmic agents have been developed to prevent or alleviate cardiac arrhythmia. For example, Class I antiarrhythmic compounds have been used to treat supraventricular arrhythmias and ventricular arrhythmias. Treatment of ventricular arrhythmia is very important since such an arrhythmia, especially ventricular fibrillation, can be fatal. Serious ventricular arrhythmias (ventricular tachycardia and ventricular fibrillation) occur most often in the presence of myocardial ischemia and/or infarction. Ventricular fibrillation often occurs in the setting of acute myocardial ischemia, before infarction fully develops. At present, lidocaine is the current drug of choice for prevention of ventricular fibrillation during acute ischemia. However, many Class I antiarrhythmic compounds may actually increase mortality in patients who have had a myocardial infarction. Therefore, there is a need in the art to identify new antiarrhythmic treatments for ventricular arrhythmias (as discussed above), as well as for atrial arrhythmias, which are also lacking suitable medical treatment. The present invention fulfills this need, and further provides other related advantages.

SUMMARY OF THE INVENTION

In one embodiment, the present invention provides cycloalkyl amine compounds of formula (I), or a solvate or pharmaceutically acceptable salt thereof:

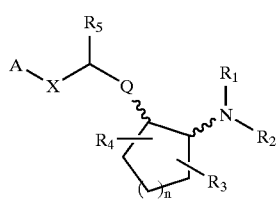

(I)

wherein, independently at each occurrence,
n is selected from 1, 3 and 4;
Q is either O (oxygen) or —O—C(O);

X is selected from a direct bond, —C($R_6$,$R_{14}$)—Y— and —C($R_{13}$)=CH—;

Y is selected from a direct bond, O, S and $C_1$–$C_4$alkylene;

$R_{13}$ is selected from hydrogen, $C_1$–$C_6$alkyl, $C_3$–$C_8$cycloalkyl, aryl and benzyl;

$R_1$ and $R_2$ are independently selected from hydrogen, C—$C_8$alkyl, $C_3$–$C_8$alkoxyalkyl, $C_1$–$C_8$hydroxyalkyl, and $C_7$–$C_{12}$aralkyl; or $R_1$ and $R_2$, when taken together with the nitrogen atom to which they are directly attached in formula (I), form a ring denoted by formula (II):

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may bear one or two substituents selected from hydrogen, hydroxy, $C_1$–$C_3$hydroxyalkyl, oxo, $C_2$–$C_4$acyl, $C_1$–$C_3$alkyl, $C_2$–$C_4$alkylcarboxy, $C_1$–$C_3$alkoxy, $C_1$–$C_{20}$alkanoyloxy, or may form a spiro five- or six-membered heterocyclic ring containing one or two heteroatoms selected from oxygen and sulfur; and any two adjacent additional carbon ring atoms may be fused to a $C_3$–$C_8$carbocyclic ring, and any one or more of the additional nitrogen ring atoms may bear substituents selected from hydrogen, $C_1$–$C_6$alkyl, $C_2$–$C_4$acyl, $C_2$–$C_4$hydroxyalkyl and $C_3$–$C_8$galkoxyalkyl; or $R_1$ and $R_2$, when taken together with the nitrogen atom to which they are directly attached in formula (I), may form a bicyclic ring system selected from 3-azabicyclo [3.2.2]nonan-3-yl, 2-azabicyclo[2.2.2]octan-2-yl, 3-azabicyclo[3.1.0]hexan-3-yl and 3-azabicyclo[3.2.0] heptan-3-yl;

$R_3$ and $R_4$ are independently attached to the cycloalkyl ring shown in formula (I) at other than the 1 and 2 positions and are independently selected from hydrogen, hydroxy, $C_1$–$C_6$alkyl and $C_1$–$C_6$alkoxy, and, when both $R_3$ and $R_4$ are attached to the same cycloalkyl ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$–$C_6$alkyl, aryl and benzyl, or $R_6$ and $R_{14}$, when taken together with the carbon to which they are attached, may form a spiro $C_3$–$C_5$cycloalkyl;

A is selected from $C_5$–$C_{12}$alkyl, a $C_3$–$C_{13}$carbocyclic ring, and ring systems selected from formulae (III), (IV), (V), (VI), (VII) and (VIII):

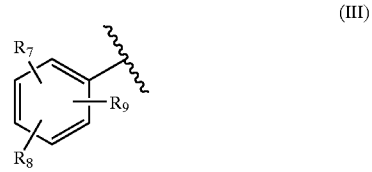

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and $N(R_{15},R_{16})$ where $R_{15}$ and $R_{16}$ are independently selected from hydrogen, acetyl, methanesulfonyl and $C_1$–$C_6$alkyl;

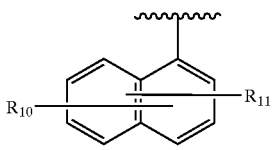

(IV)

and

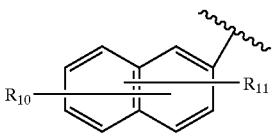

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl;

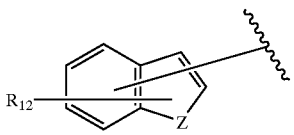

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$–$C_6$alkyl, $C_3$–$C_8$cycloalkyl, aryl and benzyl;

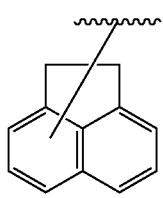

(VII)

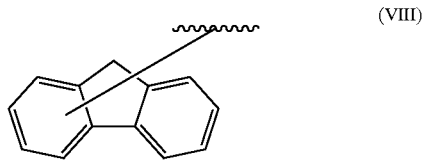

(VIII)

including isolated enantiomeric, diastereomeric and geometric isomers thereof, and mixtures thereof.

In other embodiments, the present invention provides a composition or medicament that includes a compound according to formula (I) in combination with a pharmaceutically acceptable carrier, diluent or excipient, and further provides a method for the manufacture of a composition or medicament that contains a compound according to formula (I).

In other embodiments, the present invention provides pharmaceutical compositions that contain at least one compound of formula (I) in an amount effective to treat a disease or condition in a warm-blooded animal suffering from or having the disease or condition, and/or prevent a disease or condition in a warm-blooded animal that would otherwise occur, and further contains at least one pharmaceutically acceptable carrier, diluent or excipient. The invention further provides for methods of treating a disease or condition in a warm-blooded animal suffering from or having the disease or condition, and/or preventing a disease or condition from arising in a warm-blooded animal, wherein a therapeutically effective amount of a compound of formula (I), or a composition containing a compound of formula (I) is administered to a warm-blooded animal in need thereof. The diseases and conditions to which the compounds, compositions and methods of the present invention have applicability are as follows: arrhythmia, diseases of the central nervous system, convulsions, epileptic spasms, depression, anxiety, schizophrenia, Parkinson's disease, respiratory disorders, cystic fibrosis, asthma, cough, inflammation, arthritis, allergies, gastrointestinal disorders, urinary incontinence, irritable bowel syndrome, cardiovascular diseases, cerebral or myocardial ischemias, hypertension, long-QT syndrome, stroke, migraine, ophthalmic diseases, diabetes mellitus, myopathies, Becker's myotonia, myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease or other mental disorder, and alopecia.

In another embodiment, the present invention provides a pharmaceutical composition containing an amount of a compound of formula (I) effective to produce local analgesia or anesthesia in a warm-blooded animal in need thereof, and a pharmaceutically acceptable carrier, diluent, or excipient. The invention further provides a method for producing local analgesia or anesthesia in a warm-blooded animal which includes administering to a warm-blooded animal in need thereof an effective amount of a compound of formula (I) or a pharmaceutical composition containing a compound of formula (I). These compositions and methods may be used to relieve or forestall the sensation of pain in a warm-blooded animal.

In another embodiment, the present invention provides a pharmaceutical composition containing an amount of a compound of formula (I) effective to enhance the libido in a warm-blooded animal in need thereof, and a pharmaceutically acceptable carrier, diluent, or excipient. The invention further provides a method for enhancing libido in a warm-blooded animal which includes administering to a warm-blooded animal in need thereof an effective amount of a compound of formula (I) or a pharmaceutical composition containing a compound of formula (I). These compositions and methods may be used, for example, to treat a sexual dysfunction, e.g., impotence in males, and/or to enhance the sexual desire of a patient without a sexual dysfunction. As another example, the therapeutically effective amount may be administered to a bull (or other breeding stock), to promote increased semen ejaculation, where the ejaculated semen is collected and stored for use as it is needed to impregnate female cows in promotion of a breeding program.

In another embodiment, the present invention provides a compound of formula (I) or composition containing a compound of formula (I), for use in methods for either modulating ion channel activity in a warm-blooded animal or for modulating ion channel activity in vitro.

These and other embodiments of the present invention will become evident upon reference to the following drawings and detailed description.

DETAILED DESCRIPTION OF THE INVENTION

Figure 1:
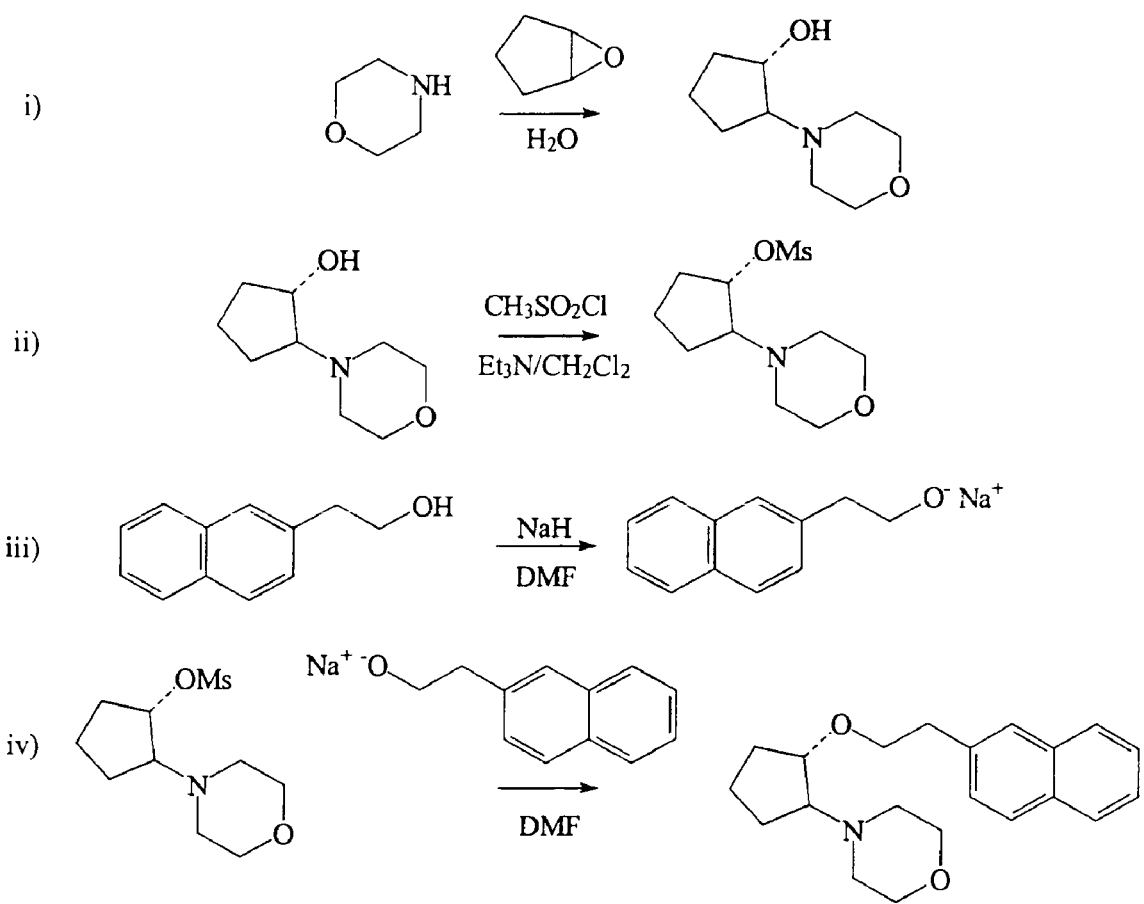
FIG. 1 illustrates a reaction sequence further described in Example 1, for preparing an aminocycloalkyl ether compound of the present invention.

As noted above, the present invention is directed to cycloalkyl amine compounds, pharmaceutical compositions containing the cycloalkyl amine compounds, and various uses for the compound and compositions. Such uses include blockage of ion channels in vitro or in vivo, the treatment of arrhythmias, the production of anesthesia, and other uses as described herein. An understanding of the present invention may be aided by reference to the following definitions and explanation of conventions used herein.

Definitions and Conventions

The compounds of the invention have either an ether oxygen atom (Q=O in formula (I)) or the non-carbonyl ester oxygen atom (Q=—O—C(O) in formula (I)) at position 1 of a cycloalkyl ring, and an amine nitrogen atom at position 2 of the cycloalkyl ring, where the cycloalkyl ring is either cyclopentyl, cycloheptyl or cyclooctyl, with other positions numbered in corresponding order as shown below in structure (A) for cyclopentane, structure (B) for cycloheptane, and structure (C) for cyclooctane:

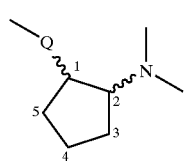
(A)

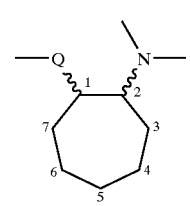
(B)

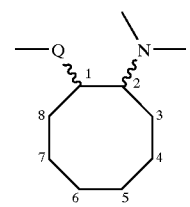
(C)

The bonds from the cycloalkyl ring to the 1-oxygen and 2-nitrogen atoms in the above formula may be relatively disposed in either a cis or trans relationship. In a preferred embodiment of the present invention, the stereochemistry of the amine and ether substituents of the cycloalkyl ring is either (R,R)-trans or (S,S)-trans. In another preferred embodiment the stereochemistry is either (R,S)-cis or (S,R)-cis.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, compounds of the invention containing the A—X—CH(R₁)-group where A equals formula (III)

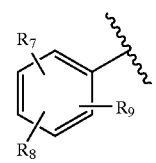
(III)

are intended to encompass compounds having the group (D):

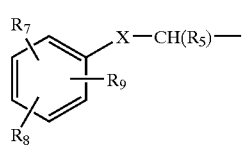
(D)

where the group (D) is intended to encompass groups wherein any ring atom that could otherwise be substituted with hydrogen, may instead be substituted with either $R_7$, $R_8$ or $R_9$, with the proviso that each of $R_7$, $R_8$ and $R_9$ appears once and only once on the ring. Ring atoms that are not substituted with any of $R_7$, $R_9$ or $R_9$ are substituted with hydrogen. In those instances where the invention specifies that a non-aromatic ring is substituted with more than one R group, and those R groups are shown connected to the non-aromatic ring with bonds that bisect ring bonds, then the R groups may be present at different atoms of the ring, or on the same atom of the ring, so long as that atom could otherwise be substituted with a hydrogen atom.

Likewise, where the invention specifies compounds containing the A—X—CH($R_5$)— group where A equals the aryl group (VI)

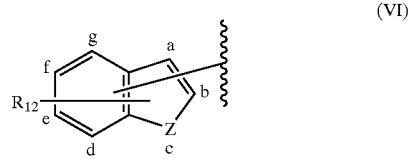

(VI)

the invention is intended to encompass compounds wherein —X—CH($R_5$)— is joined through X to the aryl group (VI) at any atom which forms the aryl group (VI) so long as that atom of group (VI) could otherwise be substituted with a hydrogen atom. Thus, there are seven positions (identified with the letters "a" through "g") in structure (VI) where the —X—CH($R_5$)— group could be attached, and it is attached at one of those seven positions. The $R_{12}$ group would occupy one and only one of the remaining six positions, and hydrogen atoms would be present in each of the five remaining positions. It is to be understood that when Z represents a divalent atom, e.g., oxygen or sulfur, then Z cannot be directly bonded to —X—CH($R_5$)—.

When the invention specifies the location of an asymmetric divalent radical, then that divalent radical may be positioned in any possible manner that provides a stable chemical structure. For example, for compounds containing the A—X—CH($R_5$)— group where X is C($R_{14}$,$R_{16}$)—Y—, the invention provides compounds having both the A—C($R_{14}$,$R_{16}$)—Y—CH($R_5$)— and A—Y—C($R_{14}$,$R_6$)—CH($R_5$)— groups.

A wavy bond from a substituent to the central cycloalkyl ring indicates that that group may be located on either side of the plane of the central ring.

The compounds of the present invention contain at least two asymmetric carbon atoms and thus exist as enantiomers and diastereomers. Unless otherwise noted, the present invention includes all enantiomeric and diastereomeric forms of the aminocycloalkyl ether compounds of the invention. Pure stereoisomers, mixtures of enantiomers and/or diastereomers, and mixtures of different compounds of the invention are included within the present invention. Thus, compounds of the present invention may occur as racemates, racemic mixtures and as individual diastereomers, or enantiomers with all isomeric forms being included in the present invention. A racemate or racemic mixture does not imply a 50:50 mixture of stereoisomers.

The phrase "independently at each occurrence" is intended to mean (i) when any variable occurs more than one time in a compound of the invention, the definition of that variable at each occurrence is independent of its definition at every other occurrence; and (ii) the identity of any one of two different variables (e.g., $R_1$ within the set $R_1$ and $R_2$) is selected without regard the identity of the other member of the set. However, combinations of substituents ard/or variables are permissible only if such combinations result in stable compounds.

In accordance with the present invention and as used herein, the following terms are defined to have following meanings, unless explicitly stated otherwise:

"Acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Acyl" refers to branched or unbranched hydrocarbon fragments terminated by a carbonyl —(C=O)— group containing the specified number of carbon atoms. Examples include acetyl [$CH_3C(O)$—, a $C_2$acyl] and propionyl [$CH_3CH_2C(O)$—, a $C_3$acyl].

"Alkanoyloxy" refers to an ester substituent wherein the non-carbonyl oxygen is the point of attachment to the molecule. Examples include propanoyloxy [($CH_3CH_2C(O)$—O—, a $C_3$alkanoyloxy] and ethanoyloxy [$CH_3C(O)$—O—, a $C_2$alkanoyloxy].

"Alkoxy" refers to an O-atom substituted by an alkyl group, for example, methoxy [—$OCH_3$, a $C_1$alkoxy].

"Alkoxyalkyl" refers to a alkylene group substituted with an alkoxy group. For example, methoxyethyl [$CH_3OCH_2CH_2$—] and ethoxymethyl ($CH_3CH_2OCH_2$—] are both $C_3$alkoxyalkyl groups.

"Alkoxycarbonyl" refers to an ester substituent wherein the carbonyl carbon is the point of attachment to the molecule. Examples include ethoxycarbonyl [$CH_3CH_2OC(O)$—, a $C_3$alkoxycarbonyl] and methoxycarbonyl [$CH_3OC(O)$—, a $C_2$alkoxycarbonyl].

"Alkyl" refers to a branched or unbranched hydrocarbon fragment containing the specified number of carbon atoms and having one point of attachment. Examples include n-propyl (a $C_3$alkyl), iso-propyl (also a $C_3$alkyl), and t-butyl (a $C_4$alkyl).

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Alkylcarboxy" refers to a branched or unbranched hydrocarbon fragment terminated by a carboxylic acid group [—COOH]. Examples include carboxymethyl [HOOC—$CH_2$—, a $C_2$alkylcarboxy] and carboxyethyl [HOOC—$CH_2CH_2$—, a $C_3$alkylcarboxy].

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds of the present invention, where phenyl and naphthyl groups are preferred carbocyclic aryl groups.

"Aralkyl" refers to an alkylene group wherein one of the points of attachment is to an aryl group. An example of an aralkyl group is the benzyl group [$C_6H_5CH_2$—, a $C_7$aralkyl group].

"Cycloalkyl" refers to a ring, which may be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present invention.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment bearing an hydroxy (—OH) group. Examples include hydroxymethyl (—CH$_2$OH, a C$_1$hydroxyalkyl) and 1-hydroxyethyl (—CHOHCH$_3$, a C$_2$hydroxyalkyl).

"Thioalkyl" refers to a sulfur atom substituted by an alkyl group, for example thiomethyl (CH$_3$S—, a C$_1$thioalkyl).

"Modulating" in connection with the activity of an ion channel means that the activity of the ion channel may be either increased or decreased in response to administration of a compound or composition or method of the present invention. Thus, the ion channel may be activated, so as to transport more ions, or may be deactivated or blocked, so that fewer or no ions, respectively, are transported by the channel.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The "therapeutically effective amount" of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

Compositions described herein as "containing a compound of formula (I)" encompass compositions that contain more than one compound of formula (I).

Compounds of the Present Invention

The compounds of the present invention are amines which may be represented by formula (I):

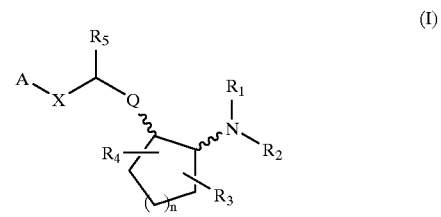

(I)

Compounds of formula (I) are cycloalkylamines such as aminocycloalkyl ethers and aminocycloalkyl esters. More specifically, these aminocycloalkyl ethers and aminocycloalkyl esters are substituted at position 2 of a cycloalkyl ring with an amine group —NR$_1$R$_2$. The C-1 position is either an ether (Q=O in formula (I)) or an ester function (Q=—O—C(O) in formula (I)). The cycloalkyl ring may also be substituted with additional substituents (designated as R$_3$ and R$_4$) as described in more detail below. In formula (I), n is selected from 1, 3 and 4, and represents a number of carbon atoms such that when n equals 1, the ring shown in Formula (I) is a substituted cyclopentane (i.e., a cyclopentyl group), when n equals 3, the ring shown in Formula (1) is a substituted cycloheptane (i.e., a cycloheptyl group), and when n equals 4, the ring shown in Formula (I) is a substituted cyclooctane (i.e., a cyclooctyl group). Examples of specific embodiments of compounds represented by formula (I) are described below.

Depending upon the selection of substituents R$_1$ and R$_2$, the compounds of formula (I) may be primary, secondary, or tertiary amines (i.e., both R$_1$ and R$_2$ are hydrogen, only one of R$_1$ and R$_2$ is hydrogen, or neither of R$_1$ and R$_2$ are hydrogen, respectively). Where the amine is tertiary, it may be a cyclic amine. Amine substituents R$_1$ and R$_2$ may be independently selected from substituents which include hydrogen, alkyl groups containing from one to eight carbon atoms (i.e., C$_1$–C$_8$alkyl), alkoxyalkyl groups containing from three to eight carbon atoms (i.e., C$_3$–C$_8$alkoxyalkyl), alkyl groups containing from one to eight carbon atoms where one of the carbon atoms is substituted with a hydroxyl group (i.e., C$_1$–C$_8$hydroxyalkyl), and aralkyl groups containing from seven to twelve carbon atoms (i.e., C$_7$–C$_{12}$aralkyl).

Alternatively, R$_1$ and R$_2$, when taken together with the nitrogen atom to which they are directly attached in formula (I), may form a ring denoted by formula (II):

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$–$C_3$hydroxyalkyl, oxo, $C_2$–$C_4$acyl, $C_1$–$C_3$alkyl, $C_2$–$C_4$alkylcarboxy, $C_1$–$C_3$alkoxy, $C_1$–$C_{20}$alkanoyloxy, or may be substituted to form a spiro five- or six-membered heterocyclic ring containing one or two heteroatoms selected from oxygen and sulfur (e.g., an acetal, thioacetal, ketal, or thioketal group); and any two adjacent additional carbon ring atoms may be fused to a $C_3$–$C_8$carbocyclic ring, and any one or more of the additional nitrogen ring atoms may be substituted with substituents selected from hydrogen, $C_1$–$C_6$alkyl, $C_2$–$C_4$acyl, $C_2$–$C_4$hydroxyalkyl and $C_3$–$C_8$alkoxyalkyl. Examples of substituents containing a fused ring system include the perhydroindolyl and 1,2,3,4-tetrahydroisoquinolinyl groups.

In connection with the ring of formula (II), any two adjacent ring atoms may be joined together by single or double bonds. Thus, the ring of formula (II) may be saturated or unsaturated, and an unsaturated ring may contain one, or more than one, sites of unsaturation. In other words, the ring of formula (II) may contain one or more double bonds, it being understood, however, that the unsaturated ring of formula (II) is chemically stable.

Alternatively, $R_1$ and $R_2$, when taken together with the 2-amino nitrogen of formula (I), may complete a bicyclic ring. Bicyclic rings include, for example, 3-azabicyclo[3.2.2]nonane, 2-azabicyclo[2.2.2]octane, 3-azabicyclo[3.1.0]hexane, and 3-azabicyclo[3.2.0]heptane. For these derivatives, the C-2 substituents of the cycloalkyl ethers of formula (I) are the following groups: 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]heptan-3-yl.

Preferably for formula (II), $R_1$ and $R_2$, when taken together, contain only a single heteroatom. Preferred heteroatoms include nitrogen, oxygen and sulfur. An example of a ring in which $R_1$ and $R_2$ together include an oxygen heteroatom is the morpholinyl group. An example of a ring where $R_1$ and $R_2$ together include a second nitrogen heteroatom is the piperazinyl group.

Cycloalkyl substituents $R_3$ and $R_4$ may be independently attached to any of the ring positions except positions 1 and 2 (e.g., both $R_3$ and $R_4$ may be attached to the same ring position or each attached to different ring positions). $R_3$ and $R_4$ are independently selected from hydrogen, hydroxy, $C_1$–$C_6$alkyl, and $C_1$–$C_6$alkoxy, and, when both $R_3$ and $R_4$ are attached to the same cycloalkyl ring atom, may together form a spiro five- or six-membered heterocyclic ring containing one or two heteroatoms selected from oxygen and sulfur. Preferred heterocyclic substituents contain either a single oxygen or a single sulfur ring atom.

Depending upon the identity of X, the ether or ester sidechain, —CH($R_5$)—X—A, in formula (I) may take several forms. For example, a compound of formula (I) may have X as a —C($R_6$,$R_{14}$)—Y— group, where Y may be any of a direct bond, an oxygen atom (O), a sulfur atom (S) or a $C_1$–$C_4$alkylene group. $R_6$ and $R_{14}$ are independently selected from hydrogen, $C_1$–$C_6$alkyl, aryl and benzyl, or $R_6$ and $R_{14}$, when taken together with the carbon to which they are attached, may form a spiro $C_3$–$C_5$cycloalkyl. Thus, compounds of the invention include compounds of formula (I) where $R_6$ and $R_{14}$ are hydrogen and Y is a direct bond, such that X may be $CH_2$.

Alternatively, X may be an alkenylene moiety, e.g., a cis- or trans-alkenylene moiety, C($R_{13}$)=CH, where $R_{13}$ may be any of hydrogen, $C_1$–$C_6$alkyl, $C_3$–$C_8$cycloalkyl, aryl or benzyl. For compounds of formula (I) where X is an alkenylene moiety, X is preferably a trans-alkenylene moiety.

Alternatively, X may be a direct bond. Independent of the selections for A, X and other variables, $R_5$ is selected from hydrogen, $C_1$–$C_6$alkyl, aryl and benzyl.

Ether or ester sidechain component A is generally a hydrophobic moiety. Typically, a hydrophobic moiety is comprised of non-polar chemical groups such as hydrocarbons or hydrocarbons substituted with halogens or ethers or heterocyclic groups containing nitrogen, oxygen, or sulfur ring atoms. Suitable hydrocarbons are $C_5$–$C_{12}$alkyl and $C_3$–$C_{13}$carbocyclic rings. Particularly preferred cyclic hydrocarbons include selected aromatic groups such as phenyl, 1-naphthyl, 2-naphthyl, indenyl, acenaphthyl, and fluorenyl and are represented by formulae (III), (IV), (V), (VI), (VII), or (VIII) respectively.

A suitable "A" group within the compounds of the present invention is a phenyl ring represented by formula (III):

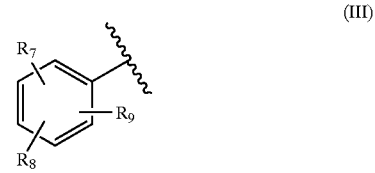

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and $N(R_{15},R_{16})$ where $R_{15}$ and $R_{16}$ are independently selected from hydrogen, acetyl, methanesulfonyl, and $C_1$–$C_6$alkyl.

For compounds of formula (I) where X is a direct bond or $CH_2$, at least one of $R_7$, $R_8$ and $R_9$ is preferably selected from amine (—$NR_{15}R_{16}$, where $R_{15}$ and $R_{16}$ are independently hydrogen, acetyl, methanesulfonyl, and $C_1$–$C_6$alkyl), bromine, chlorine, fluorine, carboxy, hydrogen, hydroxy, hydroxymethyl, nitro, trifluoromethyl, $C_2$–$C_7$alkanoyloxy, $C_1$–$C_6$alkyl, $C_1$–$C_6$alkoxy, $C_2$–$C_7$alkylcarbonyl, $C_1$–$C_6$thioalkyl or aryl groups. For compounds of formula (I) when X is CH=CH, and $R_3$ and $R_4$ are hydrogen, at least one of $R_7$, $R_8$ and $R_9$ is preferably a substituent other than hydrogen.

Other suitable "A" groups in compounds of the present invention are 1-naphthyl groups as represented by formula (IV):

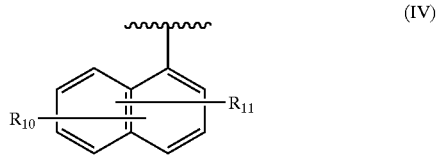

(IV)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl.

Other suitable "A" groups in compounds of the present invention are 2-naphthyl group as represented by formula (V):

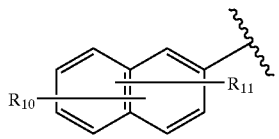

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl, as defined above.

Other suitable "A" groups in compounds of the present invention are aromatic groups represented by formula (VI):

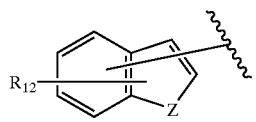

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$–$C_6$alkyl, $C_3$–$C_8$cycloalkyl, aryl and benzyl.

The aryl groups of formula (VI) are derivatives of indene, indole, benzofuran, and thianaphthene when Z is methylene, nitrogen, oxygen, and sulfur, respectively. Preferred heterocyclic groups of formula (VI) include indole where Z is NH, benzofuran where Z is O, and thianaphthene where Z is S. As described below, in a preferred embodiment, Z is O, S or N—$R_{17}$, and in a particularly preferred embodiment Z is O or S.

Another suitable "A" group in compounds of the present invention are acenaphthyl groups as represented by formula (VII):

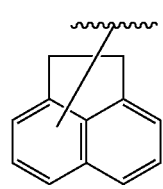

(VII)

Still another suitable "A" group in compounds of the present invention is the fluorenyl group represented by formula (VIII):

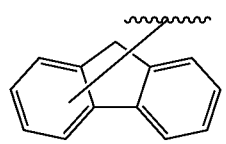

(VIII)

Preferably, ether or ester sidechain component A is an acenaphthyl or fluorenyl group only when X is a direct bond or $CH_2$. In further preferred embodiments, the acenaphthyl group is a 1-acenaphthyl group, and the fluorenyl group is a 9-fluorenyl group.

As mentioned above, the present invention provides aminocycloalkyl ethers and aminocycloalkyl esters represented by formula (I). In a preferred embodiment X is $(CH_2)$—Y. For these embodiments, Y is preferably a direct bond, an oxygen atom, or a sulfur atom. In a particularly preferred embodiment, Y is a direct bond or an oxygen atom. In another preferred embodiment Y is a direct bond and X is $C(R_6,R_{14})$, where $R_6$ and $R_{14}$ are as defined above. In another preferred embodiment, where X is $C(R_{13})$=CH, $R_{13}$ is a hydrogen atom. For these embodiments, $R_3$ and $R_4$ are preferably independently attached to the cycloalkyl ring at the 4- or 5-positions.

The following are further preferred compounds of the present invention:

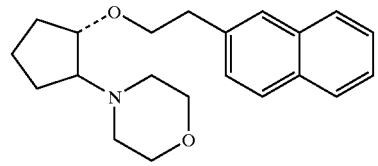

(1R,2R)/(1S,2S)-2-(4-Morpholinyl)-1-(2-naphthalenethoxy)cyclopentane monohydrochloride

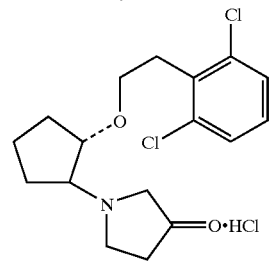

(1R,2R)/(1S,2S)-2-(3-Ketopyrrolidinyl)-1-(2,6-dichlorophenethoxy)cyclopentane monohydrochloride Outline of Method of Preparation of Compounds of the Invention The aminocycloalkyl ether compounds and the aminocycloalkyl ester compounds of the present invention contain amino and ether or ester sidechains disposed in a 1,2 arrangement on a cycloalkyl ring. Accordingly, the amino and ether or ester sidechains may be disposed in either a cis or trans relationship with respect to the plane of the cycloalkyl ring. The present invention provides synthetic methodology whereby cis or trans compounds may be prepared.

Trans compounds of the present invention may be prepared in analogy with known synthetic methodology (see, e.g., Shanklin, Jr. et al., U.S. Pat. No. 5,130,309). FIG. 1 outlines the preparation of a trans compound of the invention, which is more fully described in Example 1. As outlined in FIG. 1, the preparation of a trans compound of the invention may be carried out by a four step procedure.

In a first step (equation i) in FIG. 1), cyclopentene epoxide undergoes a ring-opening reaction with an amine. See, e.g., Szmuszkovicz, U.S. Pat. No. 4,145,435. While the reaction can occur at room temperature, typically elevated temperature is preferred in order to drive the reaction to completion in a commercially desirable length of time. The reaction is typically conducted at reflux in a solvent, such as water. Equimolar amounts of the amine and cyclopentene epoxide typically provide trails-1hydroxy 2-amino cyclopentane. A wide variety of amine compounds and substituted cyclopentene oxides may be employed in this general reaction. FIG. 1 shows an example in which morpholine is reacted with cyclopentene oxide. For amines or cyclopentene epoxides substituted with other reactive functional groups, appropriate protection groups are introduced prior to step i). Suitable protective groups are set forth in, for example, Greene, "Protective Groups in Organic Chemistry", John Wiley & Sons, New York N.Y. (1991).

In a second step (equation ii) in FIG. 1) the hydroxy group derived from the epoxide is activated or converted into a good leaving group. The leaving group illustrated in FIG. 1 is a mesylate which is preferred. However, the hydroxy group could be converted into other leaving groups according to procedures well known in the art. In a typical reaction, the aminocyclopentanol compound is treated with methanesulfonyl chloride in the presence of a base, such as triethylamine as shown in FIG. 1. The reaction is satisfactorily conducted at about 0° C. An excess of the methanesulfonyl chloride, relative to the aminocyclopentanol, is typically preferred for complete conversion of the more valuable aminocyclopentanol. For some other aminocyclopentanol compounds, it may be necessary to introduce appropriate protection groups prior to step ii) being performed. Suitable protecting groups are set forth in, for example, Greene, "Protective Groups in Organic Chemistry", John Wiley & Sons, New York N.Y. (1991).

In a third step (equation iii) in FIG. 1) an alcohol is reacted with a strong base to provide an alkoxide salt. Conversion of an alcohol to an alkoxide (also known as an alcoholate) using strong base is a reaction that will work with a wide variety of hydroxy-containing compounds. In some instances, the alcohol may have other reactive functional groups that are desirably protected prior to contact of the alcohol with strong base. Suitable protecting groups are set forth in, for example, Greene, "Protective Groups in Organic Chemistry", John Wiley & Sons, New York N.Y. (1991). Such alcohols are either commercially available or may be obtained by procedures described in the art or adapted therefrom, where suitable procedures may be identified through the Chemical Abstracts and Indices therefor, as developed and published by the American Chemical Society.

In a fourth step (equation iv) in FIG. 1), the alcoholate from iii) is reacted with the activated aminocyclopentanol from step ii) to give the ether adduct. Thus, unless protective groups must be removed, compounds of the present invention may be prepared by reacting an activated form of the appropriate 1,2-aminocycloalkanol (1 mol) with an alcoholate (1.25 mol) prepared by treatment of the selected alcohol (1.25 mol) with, for example, sodium hydride (1.3 mol). The 1,2-aminocyclopentanol (1 mol) can be activated by forming the corresponding mesylate, in the presence of methanesulfonyl chloride (1.25 mol) and triethylamine (1.5 mol). The mesylate is added quickly to the alcoholate, in a suitable solvent such as dimethylformamide. The reaction temperature is monitored carefully in order to avoid undesired side-reactions such as β-elimination. In general, a reaction temperature of 80–90° C. for 2 hours is adequate to form compounds of the invention. When the reaction has proceeded to substantial completion, the desired product is recovered from the reaction mixture by conventional organic chemistry techniques, and is purified generally by column chromatography followed by recrystallisation. Protective groups may be removed at the appropriate stage of the reaction sequence. Suitable methods are set forth in, for example, Greene, "Protective Groups in Organic Chemistry", John Wiley & Sons, New York N.Y. (1991).

The reaction sequence described above (and shown in FIG. 1) generates the aminocycloalkyl ether as the free base. The pure enantiomeric forms can be obtained by preparative chiral HPLC. The free base may be converted, if desired, to the monohydrochloride salt by known methodologies, and subsequently, if desired, to other acid addition salts by reaction with inorganic or organic salts. Acid addition salts can also be prepared metathetically by reacting one acid addition salt with an acid which is stronger than that of the anion of the initial salt.

It should be noted that aminocycloalkyl ester compounds of the present invention (formula (I) where Q is —O—C(O)—), can be prepared by standard acylation of the aminocycloalkyl alcohol formed in equation i) of FIG. 1. This is analogous to methods described in U.S. Pat. No. 5,637,583 and references cited therein.

Figure 3:
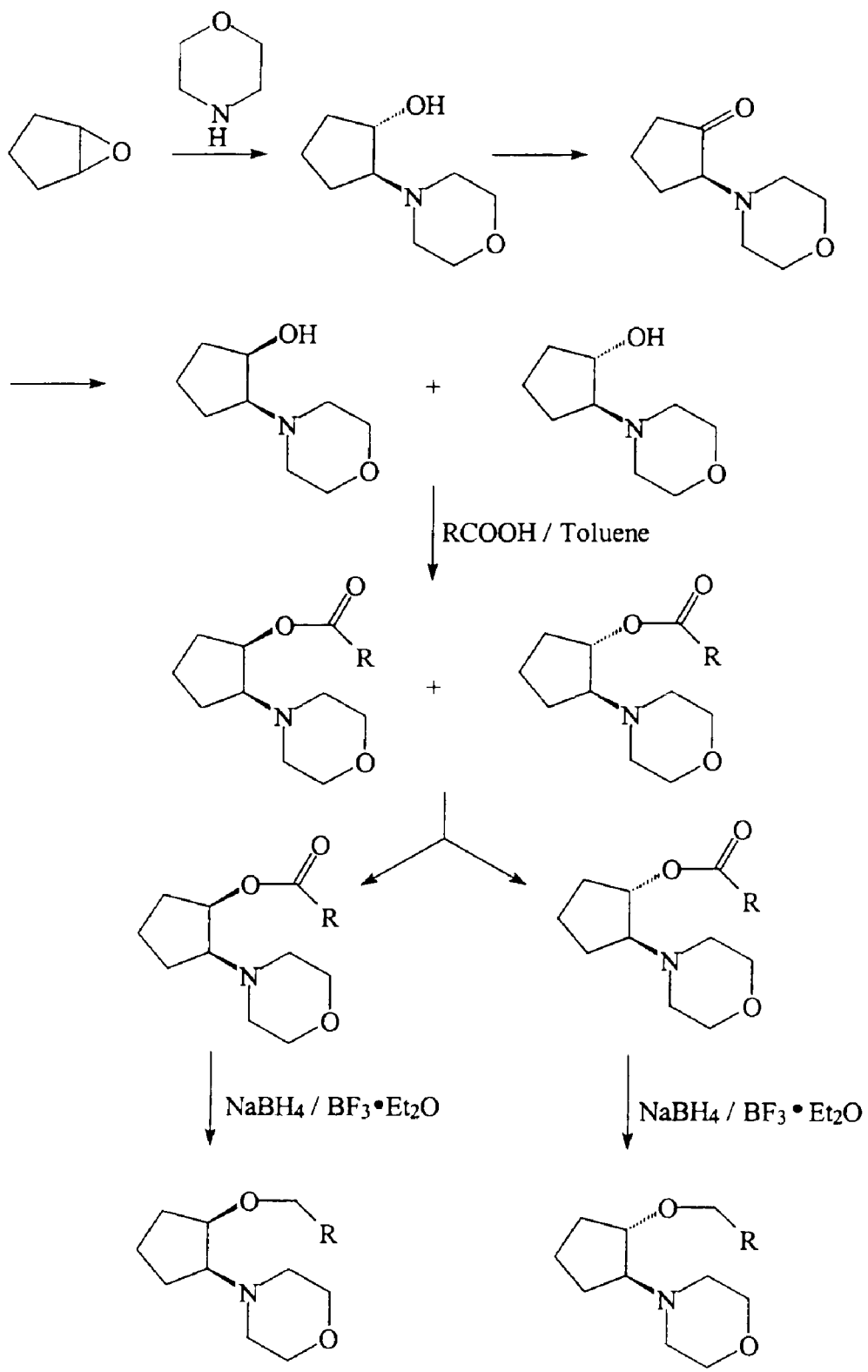
FIG. 3 illustrates a procedure whereby either cis- or trans-compounds of the present invention may be prepared.

Alternatively, cis or trans compounds of the invention may be prepared according to the chemistry outlined in FIG. 3. As shown in FIG. 3, 2-aminocyclopentanones may be prepared by Swern oxidation of the corresponding trans-1,2-aminocyclopentanol compounds (which may be prepared as described above) using oxalyl chloride/dimethyl sulfoxide (see, e.g., Synthesis 1980, 165). Subsequent reduction of the aminocyclopentanone with lithium aluminum hydride or sodium borohydride provides a mixture of cis- and trans-aminocyclopentanols. The mixture of aminoalcohols may be esterified with an appropriate carboxylic acid by azeotropic distillation in toluene in the presence of a catalytic amount of p-toluenesulfonic acid, to provide a diastereomeric mixture of cis- and trans-ester compounds of the present invention. The mixture of diastereomeric esters can be separated by preparative chromatography by one of ordinary skill in the art. The racemic cis- or trans ester could then be reduced with sodium borohydride in the presence of Lewis acid to the corresponding racemic cis- or trans-ether (see, e.g., *J. Org. Chem.* 25:875, 1960 and *Tetrahedron* 18:953, 1962). The racemic cis-ether can be resolved by preparative chiral HPLC as discussed above for the trans-compound.

The synthetic procedures described herein, especially when taken with the general knowledge in the art, provide sufficient guidance to those of ordinary skill in the art to perform the synthesis, isolation, and purification of the compounds of the present invention.

Compositions and Modes of Administration

In another embodiment, the present invention provides compositions which include a cycloalkylamine compound as described above in admixture or otherwise in association with one or more inert carriers, excipients and diluents, as well as optional ingredients if desired. These compositions are useful as, for example, assay standards, convenient means of making bulk shipments, or pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001 wt % to about 75 wt % of the entire weight of the composition. Inert carriers include any material which does not degrade or otherwise covalently react with a compound of the invention. Examples of suitable inert carriers are water; aqueous buffers, such as those which are generally useful in High Performance Liquid Chromatography (HPLC) analysis; organic solvents such as acetonitrile, ethyl acetate, hexane and the like (which are suitable for use in in vitro diagnostics or assays, but typically are not suitable for administration to a warm-blooded animal); and pharmaceutically acceptable carriers, such as physiological saline.

Thus, the present invention provides a pharmaceutical or veterinary composition (hereinafter, simply referred to as a pharmaceutical composition) containing a cycloalkylamine compound as described above, in admixture with a pharmaceutically acceptable carrier, excipient or diluent. The invention further provides a pharmaceutical composition containing an effective amount of a cycloalkylamine compound as described above, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, epidural, intrasternal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet, capsule or cachet may be a single dosage unit, and a container of cycloalkylamine compound in aerosol form may hold a plurality of dosage units.

Materials used in preparing the pharmaceutical compositions should be pharmaceutically pure and non-toxic in the amounts used. The inventive compositions may include one or more compounds (active ingredients) known for a particularly desirable effect. For instance, epinephrine may be combined with an cycloalkyl amine compound of the invention, to provide a composition useful to induce local anesthesia. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a cycloalkylamine compound as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, cachet, chewing gum, wafer, lozenges, or the like form. Such a solid composition will typically contain one or more inert diluents or edible carriers. In addition, one or more of the following adjuvants may be present: binders such as syrups, acacia, sorbitol, polyvinylpyrrolidone, carboxymethylcellulose, ethyl cellulose, microcrystalline cellulose, gum tragacanth or gelatin, and mixtures thereof; excipients such as starch, lactose or dextrins, disintegrating agents such as alginic acid, sodium alginate. Primogel, corn starch and the like; lubricants such as magnesium stearate or Sterotex; fillers such as lactose, mannitols, starch, calcium phosphate, sorbitol, methylcellulose, and mixtures thereof; lubricants such as magnesium stearate, high molecular weight polymers such as polyethylene glycol, high molecular weight fatty acids such as stearic acid, silica, wetting agents such as sodium lauryl sulfate, glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, aqueous or oily emulsion or suspension, or even dry powders which may be reconstituted with water and/or other liquid media prior to use. The liquid may be for oral administration or for delivery by injection, as two examples. When intended for oral administration, preferred compositions contain, in addition to the present compounds, one or more of a sweetening agent, thickening agent, preservative (e.g., alkyl p-hydoxybenzoate), dye/colorant and flavor enhancer (flavorant). In a composition intended to be administered by injection, one or more of a surfactant, preservative (e.g., alkyl p-hydroxybenzoate), wetting agent, dispersing agent, suspending agent (e.g., sorbitol, glucose, or other sugar syrups), buffer, stabilizer and isotonic agent may be included. The emulsifying agent may be selected from lecithin or sorbitol monooleate.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid compositions intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active cycloalkylamine compound. Preferred compositions and preparations according to the present invention are prepared so that a parenteral dosage unit contains between 0.01 to 10% by weight of active compound.

The pharmaceutical composition may be intended for topical administration, in which case the carrier may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 25% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the cycloalkylamine compound is dispersed homogeneously therein by stirring. The molten homogeneous mixture is then poured into convenient sized molds, allowed to cool and thereby solidify.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The composition in solid or liquid form may include an agent which binds to the cycloalkylamine compound and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in methods for either modulating ion channel activity in a warm-blooded animal or for modulating ion channel activity in vitro, or used in the treatment of arrhythmia, diseases of the central nervous system, convulsion, epileptic spasms, depression, anxiety, schizophrenia, Parkinson's disease, respiratory disorders, cystic fibrosis, asthma, cough, inflammation, arthritis, allergies, gastrointestinal disorders, urinary incontinence, irritable bowel syndrome, cardiovascular diseases, cerebral or myocardial ischemias, hypertension, long-QT syndrome, stroke, migraine, ophthalmic diseases, diabetes mellitus, myopathies, Becker's myotonia, myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease and other mental disorders, and alopecia. Other agents known to cause libido enhancement, local analgesia or anesthesia may be combined with compounds of the present invention.

The pharmaceutical compositions may be prepared by methodology well known in the pharmaceutical art. The aminocycloalkyl compounds of the invention may be in the form of a solvate in a pharmaceutically acceptable solvent such as water or physiological saline. Alternatively, the compounds may be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability or stability of the compound for the appropriate mode of employment (e.g., oral or parenteral routes of administration).

A composition intended to be administered by injection can be prepared by combining the cycloalkylamine compound with water, and preferably buffering agents, so as to form a solution. The water is preferably sterile pyrogen-free water. A surfactant may be added to facilitate the formation of a homogeneous solution or suspension. Surfactants are compounds that non-covalently interact with the cycloalkylamine compound so as to facilitate dissolution or homogeneous suspension of the cycloalkylamine compound in the aqueous delivery system. Surfactants are desirably present in aqueous compositions of the invention because the cycloalkylamine compounds of the present invention are typically hydrophobic. Other carriers for injection include, without limitation, sterile peroxide-free ethyl oleate, dehydrated alcohols, propylene glycol, as well as mixtures thereof.

Suitable pharmaceutical adjuvants for the injecting solutions include stabilising agents, solubilising agents, buffers, and viscosity regulators. Examples of these adjuvants include ethanol, ethylenediaminetetraacetic acid (EDTA), tartrate buffers, citrate buffers, and high molecular weight polyethylene oxide viscosity regulators. These pharmaceutical formulations may be injected intramuscularly, epidurally, intraperitoneally, or intravenously.

Pharmacological Testing

As noted above, the present invention provides for utilising the compounds described above in in vitro and in vivo methods. In one embodiment, ion channels, such as cardiac sodium channels, are blocked in vitro or in vivo.

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

Accordingly, compounds that are capable of modulating the activity or function of the appropriate ion channels will be useful in treating or preventing a variety of diseases or disorders caused by defective or inadequate function of the ion channels. The compounds of the invention are found to have significant activity in modulating ion channel activity both in vivo and in vitro.

Thus, the present invention provides for methods of treating a disease or condition in a warm-blooded animal suffering from or having the disease or condition, and/or preventing a disease or condition from arising in a warm-blooded animal, wherein a therapeutically effective amount of a compound of formula (I), or a composition containing a compound of formula (I) is administered to a warm-blooded animal in need thereof. The diseases and conditions to which the compounds, compositions and methods of the present invention may be applied are as follows: arrhythmia, diseases of the central nervous system, convulsion, epileptic spasms, depression, anxiety, schizophrenia, Parkinson's disease, respiratory disorders, cystic fibrosis, asthma, cough, inflammation, arthritis, allergies, gastrointestinal disorders, urinary incontinence, irritable bowel syndrome, cardiovascular diseases, cerebral or myocardial ischemias, hypertension, long-QT syndrome, stroke, migraine, ophthalmic diseases, diabetes mellitus, myopathies, Becker's myotonia, myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease or other mental disorder, and alopecia.

Furthermore, the present invention provides a method for producing local analgesia or anesthesia in a warm-blooded animal which includes administering to a warm-blooded animal in need thereof an effective amount of a compound of formula (I) or a pharmaceutical composition containing a compound of formula (I). These methods may be used to relieve or forestall the sensation of pain in a warm-blooded animal.

Furthermore, the present invention provides a method wherein a preparation that contains ion channels is exposed to, or a warm-blooded animal (e.g., a mammal, such as a human) is administered an effective amount of an aminocycloalkyl ether compound of the invention. Suitable preparations containing cardiac sodium channels include cells isolated from cardiac tissue as well as cultured cell lines. Treatment of such a preparation would entail, for example, incubation of the ion channels with a compound under conditions and for a time sufficient to permit modulation of the activity of the channels by the compound.

In another embodiment, the compounds described above are provided for treating arrhythmia. As used herein, "treating arrhythmia" refers to both therapy for arrhythmia and for the prevention of arrhythmias occurring in a heart that is susceptible to arrhythmia. An effective amount of a composition of the present invention is used to treat arrhythmia in a warm-blooded animal, such as a human. Methods of administering effective amounts of antiarrhythmic agents are well known in the art and include the administration of an oral or parenteral dosage form. Such dosage forms include but are not limited to, parenteral dosage form. Such dosage forms include, but are not limited to, parenteral solutions, tablets, capsules, sustained release implants, and transdermal delivery systems. Generally, oral or intravenous administration is preferred. The dosage amount and frequency are selected to attain effective levels of the agent without harmful effects. It will generally range from a dosage of from about 0.1 to about 100 mg/kg/day, and typically from about 0.1 to 10 mg/kg where administered orally or intravenously for antiarrhythmic effect.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an aminocycloalkyl ether compound of the invention may be co-administered with epinephrine in order to include local anesthesia.

In order to assess whether a compound of the present invention has a desired pharmacological activity, it is subjected to a series of tests. The precise test to employ will depend on the physiological response of interest. The published literature contains numerous protocols for testing the efficacy of a potential therapeutic agent, and these protocols may be employed with the present compounds and compositions.

For example, in connection with treatment or prevention of arrhythmia, a series of four tests may be conducted. In the first of these tests, a compound of the present invention is given as increasing (doubling with each dose) intravenous boluses every 8 minutes to a pentobarbital anesthetized rat. The effects of the compound on blood pressure, heart rate and the ECG are measured at 30 seconds, 1, 2, 4 and 8 minutes after each dose. Increasing doses are given until the animal dies. The cause of death is identified as being of either respiratory or cardiac origin. This test gives an indication as to whether the compound is modulating the activity of sodium channels and/or potassium channels, and in addition gives information about acute toxicity. The indices of sodium channel blockade are increasing P-R interval and QRS widening of the ECG. Potassium channel blockade results in Q-T interval prolongation of the ECG.

A second test involves administration of a compound as an infusion to pentobarbital anesthetized rats in which the left ventricle is subjected to electrical square wave stimulation performed according to a preset protocol described in further detail below. This protocol includes the determination of thresholds for induction of extrasystoles and ventricular fibrillation. In addition, effects on electrical refractoriness are assessed by a single extra beat technique. In addition effects on blood pressure, heart rate and the ECG are recorded. In this test, sodium channel blockers produce the ECG changes expected from the first test. In addition, sodium channel blockers also raise the thresholds for induction of extrasystoles and ventricular fibrillation. Potassium channel blockade is revealed by increasing refractoriness and widening of the Q-T intervals of the ECG.

A third test involves exposing isolated rat hearts to increasing concentrations of a compound. Ventricular pressures, heart rate, conduction velocity and ECG are recorded in the isolated heart in the presence of varying concentrations of the compound. The test provides evidence for direct toxic effects on the myocardium. Additionally, selectivity, potency and efficacy of action of a compound can be ascertained under conditions simulating ischemia. Concentrations found to be effective in this test are expected to be efficacious in the electrophysiological studies.

A fourth test is estimation of the antiarrhythmic activity of a compound against the arrhythmias induced by coronary artery occlusion in anaesthetized rats. It is expected that a good antiarrhythmic compound will have antiarrhythmic activity at doses which have minimal effects on either the ECG, blood pressure or heart rate under normal conditions and preferably on all these parameters.

All of the foregoing tests are performed using rat tissue. In order to ensure that a compound is not having effects which are only specific to rat tissue, further experiments are performed in dogs and primates. In order to assess possible sodium channel and potassium channel blocking action in vivo in dogs, a compound is tested for effects on the ECG, ventricular epicardial conduction velocity and responses to electrical stimulation. An anesthetized dog is subjected to an open chest procedure to expose the left ventricular epicardium. After the pericardium is removed from the heart a recording/stimulation electrode is sewn onto the epicardial surface of the left ventricle. Using this array, and suitable stimulation protocols, conduction velocity across the epicardium as well as responsiveness to electrical stimulation can be assessed. This information coupled with measurements of the ECG allows one to assess whether sodium and/or potassium channel blockade occurs. As in the first test in rats, a compound is given as a series of increasing bolus doses. At the same time possible toxic effects of a compound on the dog's cardiovascular system are assessed.

The effects of a compound on the ECG and responses to electrical stimulation are also assessed in intact, halothane anesthetized baboons (*Papio anubis*). In this preparation, a blood pressure cannula and ECG electrodes are suitably placed in an anesthetized baboon. In addition, a stimulating electrode is placed into the right ventricle, together with a monophasic action potential electrode. As in the tests described above, ECG and electrical stimulation response to a compound reveal the possible presence of sodium and/or potassium channel blockade. The monophasic action potential also reveals whether a compound widens the action potential, an action expected of a potassium channel blocker.

As another example, in connection with the mitigation or prevention of the sensation of pain, the following test may be performed. To determine the effects of a compound of the present invention on an animal's response to a sharp pain sensation, the effects of a slight prick from a 7.5 g weighted syringe fitted with a 23 G needle applied to the shaved back of a guinea pig (*Cavia porcellus*) is assessed following subcutaneous administration of a solution of the compound in saline (e.g., 50 μl, 10 mg/ml) to raise a visible bleb on the skin. Each test is performed on the central area of the bleb and also on its periphery to ascertain the diffusion of the test solution from the point of administration. If the test animal produces a flinch in response to the stimulus, this demonstrates the absence of blockade of pain sensation. Testing is performed at intervals for up to 4 hours post administration. The sites of bleb formation are examined after 24 hours and showed no skin abnormalities arise from the local administration of test substances or the vehicle used in the preparation of the test solutions.

Other Compositions

The present invention also provides kits that contain a pharmaceutical composition which includes one or more compounds of the above formulae. The kit also includes instructions for the use of the pharmaceutical composition for modulating the activity of ion channels, for the treatment of arrhythmia or for the production of local analgesia and/or anesthesia, and for the other utilities disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

The following examples are offered by way of illustration and not by way of limitation. In the Examples, and unless otherwise specified, starting materials were obtained from well-known commercial supply houses, e.g., Aldrich Chemical Company (Milwaukee, Wis.), and were of standard grade and purity. "Ether" and "ethyl ether" both refer to diethyl ether: "h." refers to hours; "min." refers to minutes: "GC" refers to gas chromatography: "v/v" refers to volume per volume; and ratios are weight ratios unless otherwise indicated.

EXAMPLES

Example 1

(1R,2R)/(1S,2S)-2-(4-MORPHOLINYL)-1-(2-NAPHTHALENETHOXY)CYCLOPENTANE MONOHYDROCHLORIDE (COMPOUND #1)

The following reaction sequence is illustrated in FIG. 1.

i) (1R,2R)/(1S,2S)-2-(4-Morpholinyl)cyclopentanol: A mixture of morpholine (15.0 ml, 172 mmol) and cyclopentene oxide (15 ml, 172 mmol) in water (5 ml) was refluxed for 3 hours. The cooled reaction mixture was then partitioned between 40% NaOH aqueous solution (100 ml) and diethyl ether (100 ml). The aqueous layer was extracted twice more with diethyl ether (2×50 ml). The combined organic layers were dried over sodium sulfate and the solvent was evaporated in vacuo. Vacuum distillation provided 20.6 g of the title compound.

ii) (1R,2R)/(1S,2S)-2-(4-Morpholinyl)-1-(2-naphthalenethoxy)cyclopentane monohydrochloride: To a chilled (0° C.) solution of (1R,2R)/(1S,2S)-2-(4-morpholinyl)cyclopentanol (2.77 g, 16.20 mmol) and triethylamine (3.4 ml, 24.00 mmol) in dichloromethane (50 ml) was added via cannula a solution of methanesulfonyl chloride (1.55 ml, 20.00 mmol) in dichloromethane (50 ml). The reaction mixture was stirred for another hour at 0° C. and then at room temperature for 4 hours. The reaction mixture was washed with water (2×50 ml) and the combined aqueous washings back-extracted with dichloromethane (50 ml). The combined organic layers were dried over sodium sulfate and concentrated in vacuo to provide 4.0 g of the crude mesylate.

iii) Sodium hydride, 80% oil dispersion (0.60 g, 25.00 mmol), was washed with hexanes (3×10 ml), and then suspended in anhydrous dimethylformamide (50 ml). To this suspension was added via cannula a solution of 2-naphthalenecthanol (3.4 g, 20.00 mmol) in anhydrous dimethylformamide (50 ml). The reaction mixture was stirred at room temperature for one hour.

iv) The mesylate dissolved in dimethylformamide (50 ml) was added quickly to the alkoxide mixture (iii). The reaction mixture was heated at 85° C. for 2 hours, and then at 45° C. overnight. The reaction mixture was poured into iced water (800 ml) and extracted with ethyl acetate (3×200 ml). The combined organic extracts were back-washed with a saturated aqueous sodium chloride solution (300 ml) and dried over sodium sulfate. Evaporation of the solvent in vacuo provided 6.7 g of oil, which was dissolved in 1M HCl aqueous solution (50 ml) and water (150 ml). The acidic aqueous solution was extracted with diethyl ether (2×100 ml) and then adjusted to pH 10 with 50% aqueous sodium hydroxide solution. The basic aqueous solution was extracted with ethyl ether (2×100 ml) and the combined organic layers were dried over sodium sulfate and concentrated in vacuo to give 1.47 g of the crude free aminoether. The crude product was purified by chromatography column using silica gel 60, (230–400 mesh, BDH Inc.) and a mixture of 3% methanol in dichloromethane as eluent. The purified product was dissolved in diethyl ether (50 ml) and converted to the monohydrochloride salt by the addition of ethereal HCl (50 ml). The solvent was evaporated in vacuo; the residue dissolved in the minimum amount of warm absolute ethanol and diethyl ether was added in order to trigger crystallisation. The crystals were collected yielding 0.29 g of the title compound.

Compound number 1 has a calculated molecular weight of 361.91, and provided elemental analysis as set forth in Table 1.

Example 2

(1R,2R)/(1S,2S)-2-(3-KETOPYRROLIDINYL)-1-(2,6-DICHLOROPHENETHOXY)CYCLOPENTANE MONOHYDROCHLORIDE (COMPOUND #2)

Figure 2A:
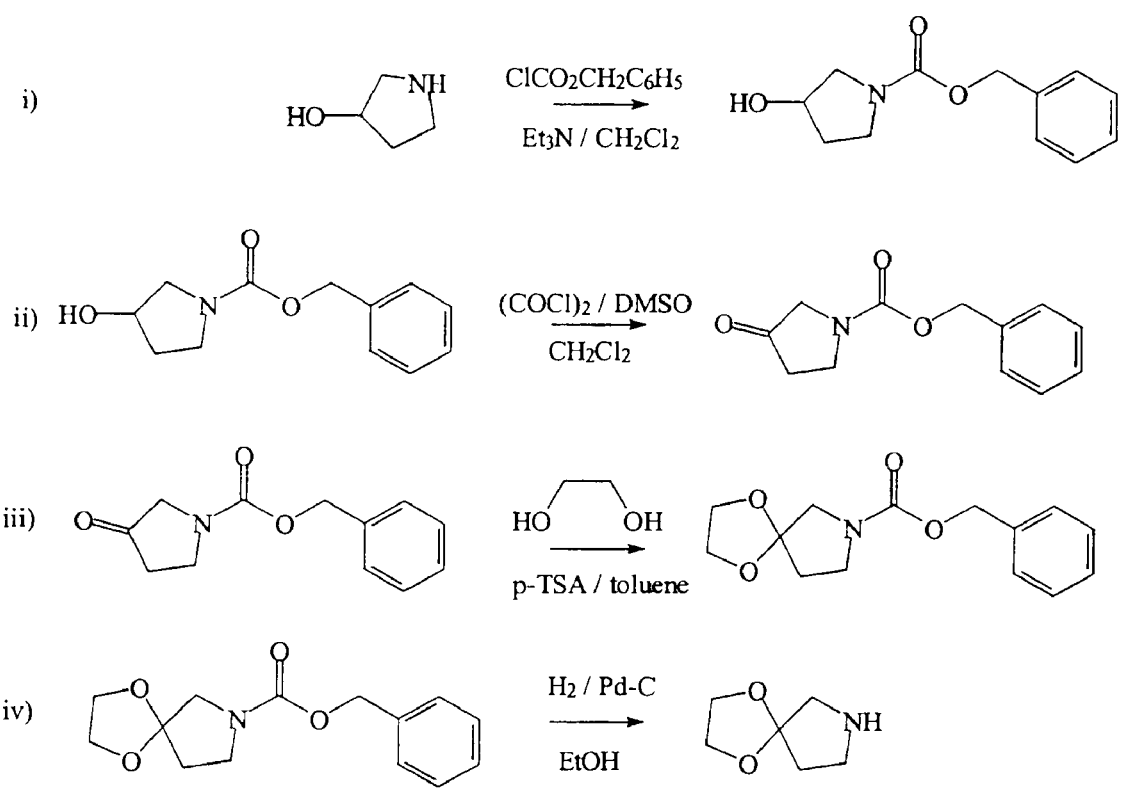
FIGS. 2A and 2B illustrate a reaction sequence further described in Example 2 for preparing an aminocycloalkyl ether compound of the present invention.
Figure 2B:
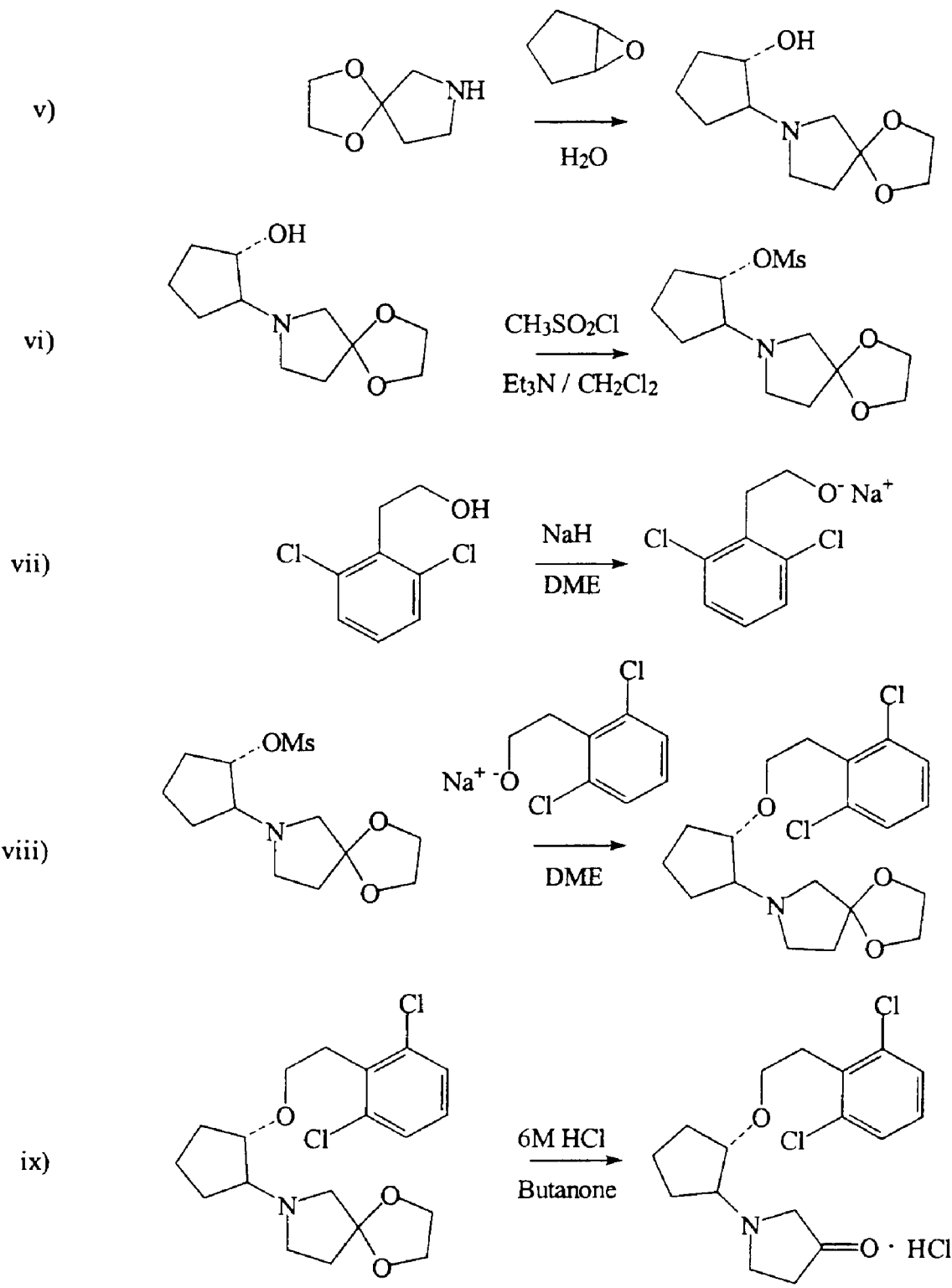

The following reaction sequences are illustrated in FIGS. 2A and 2B.

i) N-Benzyloxycarbonyl-3-pyrrolidinol: To a chilled (–60° C.), stirred solution of (R)-(+)-3-pyrrolidinol (20.0 g, 98%, 224.9 mmol) and triethylamine (79.2 ml, 99%, 562 mmol) in dichloromethane (200 ml) was added dropwise over 45 min., a solution of benzyl chloroformate (33.8 ml, 95%, 224.9 mmol) in dichloromethane (80 ml). The reaction mixture (a yellow suspension) was allowed to warm up to room temperature and was stirred under argon at room temperature overnight. The reaction mixture was then quenched with 1M aqueous HCl solution (350 ml) and the organic layer was collected. The acidic aqueous layer was extracted with dichloromethane (2×150 ml) and the combined organic layers were dried over sodium sulfate. Evaporation in vacuo of the solvent provided 59.62 g of pale yellow oil, which was subjected to high vacuum for 15 min. to yield 58.23 g (17% over theoretical yield) of the crude title compound which was suitable for use in the next step without any further purification.

ii) N-Benzyloxycarbonyl-3-pyrrolidinone: To a chilled (–60° C.), stirred solution of oxalyl chloride (23 ml, 98%, 258.6 mmol) in dichloromethane (400 ml) was added dropwise a solution of anhydrous dimethyl sulfoxide (36.7 ml, 517.3 mmol) in dichloromethane (20 ml) at a rate that the temperature remained below –40° C. The reaction mixture was then stirred at –60° C. for 15 min. Then a solution of N-benzyloxycarbonyl-3-pyrrolidinol (58.22 g, no more than 224.9 mmol) in dichloromethane (80 ml) was added dropwise, keeping the reaction mixture temperature below –50° C. The reaction mixture was then stirred at –60° C. for 30 min. before triethylamine (158.3 ml, 99%, 1.125 mol) was added. The resultant mixture was allowed to warm up to room temperature and then washed successively with water (600 ml), 1M aqueous HCl solution (580 ml) and water (400 ml). The organic layer was dried over sodium sulfate and concentrated in vacuo to give 54.5 g of amber oil, which was stirred under high vacuum at room temperature for 25 min. to give 52.08 g of the crude title compound which was suitable for use in the next step without further purification.

iii) 7-Benzyloxycarbonyl-1,4-dioxa-7-azaspiro [4,4] nonane: A mixture of N-benzyloxycarbonyl-3-pyrrolidinone (51.98 g. 224.9 mmol), ethylene glycol (18.8 ml, 99+%, 337.4 mmol) and p-toluenesulfonic acid monohydrate (1.04 g, 5.4 mmol) in toluene (180 ml) was refluxed in a Dean & Stark apparatus for 16 hours. The reaction mixture was then diluted with more toluene (250 ml) and washed with saturated aqueous sodium bicarbonate solution (150 ml) and saturated aqueous sodium chloride solution (2×150 ml). The combined aqueous layers were back-extracted with toluene (100 ml). The combined organic layers were dried over sodium sulfate and concentrated in vacuo to give 79.6 g of dark oil. A solution of the crude product in ethanol (500 ml) was decolorized by elution through a bed of activated carbon (80 g). The charcoal was washed with more ethanol (1000 ml) and toluene (500 ml). The filtrate was concentrated in vacuo and subjected to high vacuum for 1 hour to yield 63.25 g of the crude title compound which was suitable for the next step without any further purification.

iv) 1,4-Dioxa-7-aspiro[4.4]nonane: A mixture of 7-benzyloxycarbonyl-1,4-dioxa-7-azaspiro[4,4]nonane (34.79 g. no more than 123.7 mmol) and 10% Pd-C (13.9 g) in ethanol (90 ml) was agitated under hydrogen (60 psi) in a Parr apparatus at room temperature for 1.5 hour. The catalyst was filtered off, the solvent was evaporated in vacuo and the residue was subjected to high vacuum for 20 min. to yield 15.86 g of the title compound (yield 99.3%).

v) (1R,2R)/(1S,2S)-2-(1,4-Dioxa-7-azaspiro[4,4]non-7-yl)cyclopentanol: A mixture of 1,4-dioxa-7-azaspiro[4,4]nonane (5.17 g, 40 mmol), cyclopentene oxide (8.54 ml, 96 mmol) and water (1.7 ml) was heated at 80° C. for 2 hours. The reaction mixture was then partitioned between 40% aqueous sodium hydroxide solution (15 ml) and diethyl ether (30 ml). The basic aqueous layer was extracted twice more with diethyl ether (2×30 ml). The combined organic extracts were dried over sodium sulfate and concentrated in vacuo. The residue was stirred under high vacuum at 50° C. for 1 hour (to remove the excess of cyclopentene oxide) to yield 7.13 g of the crude title compound (yield 83.5%).

vi) (1R,2R)/(1S,2S)-2-[1,4-Dioxa-7-azaspiro[4,4]non-7-yl]-1-(2,6-dichlorophenethoxy)cyclopentane: To a chilled (0° C.), stirred solution of (1R,2R)/(1S,2S)-2-(1,4-Dioxa-7-azaspiro[4,4]non-7-yl)cyclopentanol (1.88 g, 8.8 mmol) and triethylamine (1.16 g, 11.44 mmol) in dichloromethane (240 ml) was added dropwise methanesulfonyl chloride (0.9 ml, 11.44 mmol). The reaction mixture was stirred at 0° C. for 45 min. and then at room temperature for 3 hours. The reaction mixture was then washed with a mixture (1:1, v/v. 12 ml) of water and saturated aqueous sodium bicarbonate solution. The aqueous layer was back-extracted with dichloromethane (10 ml). The combined organic extracts were dried over sodium sulfate, the solvent was evaporated in vacuo and the residue was subjected to high vacuum for 4 hours to yield the crude mesylate suitable for the next step without any further purification.

vii) To sodium hydride (323 mg, 10.56 mmol) suspended in anhydrous (freshly distilled from sodium) ethylene glycol dimethyl ether (20 ml) was added a solution of 2,6-dichlorophenethanol (2.01 g, 10.56 mmol) in anhydrous* ethylene glycol dimethyl ether (10 ml). The resultant mixture was then stirred at room temperature for 3 hours.

viii) A solution of mesylate (vi) in anhydrous* ethylene glycol dimethyl ether (10 ml) was added quickly to the alkoxide (vii) and the resulting mixture was readily heated to reflux under argon for 16 hours. The organic solvent was evaporated in vacuo and to the residue was added water (50 ml). The aqueous solution was acidified with 10% HCl aqueous solution to pH 0.5. The acidic aqueous layer was extracted with diethyl ether (2×30 ml) in order to extract unreacted 2,6-dichlorophenethanol. The pH of the aqueous solution was adjusted to pH 5.0 with 5M NaOH aqueous solution and then extracted with diethyl ether (2×50 ml). The combined organic extracts were dried over sodium sulfate and the solvent was evaporated in vacuo to yield 2.2 g of the title compound which was suitable for the next step without any further purification.

ix) (1R,2R/(1S,2S)-2-(3-Ketopyrrolidinyl)-1-(2,6-dichlorophenethoxy)cyclopentane monohydrochloride: A solution of (1R,2R)/(1S,2S)-2-[1,4-dioxa-7-azaspiro[4,4]non-7-yl]-1-(2,6-dichlorophenethoxy)cyclohexane (2.2 g) with 6M HCl aqueous solution (20 ml) in 2-butanone (80 ml) was refluxed for 12 hours. The butanone was evaporated in vacuo and the residual aqueous solution was diluted with water (100 ml). The aqueous solution was extracted with diethyl ether (2×50 ml) and then with dichloromethane (3×50 ml). The pooled dichloromethane extracts were dried over sodium sulfate and the solvent was evaporated in vacuo. The residual oil was azeotropically dried with toluene. The resulting sticky product was vigorously stirred overnight in diethyl ether (150 ml) with occasional scratching to trigger crystallisation of the title compound (1.9 g, 57%).

Compound number two had a calculated molecular weight of 378.73, and provided the elemental analysis data set forth in Table 1.

TABLE 1

| Compound | Formula | Calculated | Found |
|---|---|---|---|
| #1 | $C_{21}H_{28}NO_2Cl$ | C 69.69, H 7.80, N 3.87% | C 69.23, H 7.71, N 3.83% |
| #2 | $C_{17}H_{22}NO_2Cl_3$ | C 53.91, H 5.86, N 3.70% | C 54.13, H 5.68, N 3.58% |

Example 3

ASSESSMENT OF ANTIARRHYTHMIC EFFICACY

Antiarrhythmic efficacy was assessed by investigating the effect of a compound on the incidence of cardiac arrhythmias in conscious rats subjected to coronary artery occlusion. Rats weighing 200–300 gms were subjected to preparative surgery and assigned to groups in a random block design. In each case, the animal was anesthetized with halothane during surgical preparation. The left femoral artery was cannulated for measurement of mean arterial blood pressure and withdrawal of blood samples. The left femoral vein was also cannulated for injection of drugs. The thoracic cavity was opened and a polyethylene occluder loosely placed around the left anterior descending coronary artery. The thoracic cavity was then closed. ECG was recorded by insertion of electrodes placed along the anatomical axis of the heart. All cannulae and electrode leads were exteriorized in the mid scapular region. In a random and double-blind manner, about 0.5 to 2 hours post-surgery, an infusion of vehicle, or the compound to be tested was given. After 5–15 minutes infusion, the occluder was pulled so as to produce coronary artery occlusion. ECG, arrhythmias, blood pressure, heart rate and mortality were monitored for 30 minutes after occlusion. Arrhythmias were recorded as ventricular tachycardia (VT) and ventricular fibrillation (VF) and scored according to Curtis, M. J. and Walker, M. J. A., *Cardiovasc. Res.* 22:656 (1988) (see Table 2).

TABLE 2

| Score | Description |
|---|---|
| 0 | 0–49 VPBs |
| 1 | 50–499 VPBs |
| 2 | >499 VPBs and/or 1 episode of spontaneously reverting VT or VF |
| 3 | >1 episode of VT or VF or both (>60 s total combined duration) |
| 4 | VT or VF or both (60–119 s total combined duration) |
| 5 | VT or VF or both (>119 s total combined duration) |
| 6 | fatal VF starting at >15 min after occlusion |
| 7 | fatal VF starting at between 4 min and 14 min 59 s after occlusion |
| 8 | fatal VF starting at between 1 min and 3 min 59 s after occlusion |
| 9 | fatal VF starting <1 min after occlusion |

Where:
VPB = ventricular premature beats
VT = ventricular tachycardia
VF = ventricular fibrillation Rats were excluded from the study if they did not exhibit pre-occlusion serum potassium concentrations within the range of 2.9–3.9 mM. Occlusion is associated with increases in R-wave height and "S-T" segment elevation: and an occluded zone (measured after death by cardiogreen dye perfusion) in the range of 25%–50% of total left-ventricular weight.

Table 3 describes the result of tests of the compounds described therein as values of a given infusion rate in micromol/kg/min. ($ED_{50}AA$) which will reduce the arrhythmia score in treated animals to 50% of that shown by animals treated only with the vehicle in which the test drug(s) is dissolved.

TABLE 3

| Compound | $ED_{50}AA$ |
|---|---|
| #1 | 1.5 |
| #2 | 4 |

Example 4

MEASUREMENT OF ECG PARAMETERS

Rats weighing 200–250 gms were used in this example. Animals were anesthetized with 60 mg/kg pentobarbital i.p. The carotid artery and jugular vein were cannulated for measurement of blood pressure and drug injection, respectively. ECG was recorded by insertion of electrodes placed along the anatomical axis of the heart. All compounds were given as bolus injections.

Various ECG parameters were measured. Table 4 describes the results of the tests as $ED_{25}$ (micromol/kg) which are the doses required to produce a 25% increase in the parameter measured (NE=not estimated). The increases in P—R interval and QRS interval indicate cardiac sodium channel blockage while the increase in Q-T interval indicates ancillary cardiac potassium channel blockage which is the property of a type 1a antiarrhythmic.

TABLE 4

| Compound | PR | QRS | QT |
|---|---|---|---|
| #1 | 45 | 37 | 2.5 |
| #2 | NE | 9 | 3.3 |

NE = Not Estimated

Example 5

ASSESSMENT OF SODIUM CHANNEL BLOCKAGE

Rats were prepared according to the preceding procedure. Two silver stimulating electrodes were inserted through the chest wall and implanted in the left ventricle. Square wave stimulation was used to determine threshold current for capture, ventricular fibrillation threshold current, and effective refractory period (Howard, P. G. and Walker, M. J. A., Proc. West. Pharmacol. Soc. 33:123–127 (1990)). Table 5 contains $ED_{25}$ values for these indices of cardiac sodium channel blockage, where the $ED_{25}$ is the infusion rate in micromol/kg/minute of compound required to elicit a 25% increase from control. The increases in refractoriness indicate ancillary blockage of potassium channels. The threshold current for capture is represented by "It". The fibrillation threshold current is represented by "VFT". The effective refracting period is represented by "ERP".

TABLE 5

| Compound | It | VFT | ERP |
|---|---|---|---|
| #1 | 3.3 | 1.3 | 2.5 |
| #2 | 10 | NE | 2.6 |

NE = Not Estimated

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A composition comprising a compound of formula (I), or a solvate or pharmaceutically acceptable salt thereof:

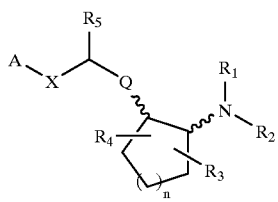

(I)

wherein, independently at each occurrence,
n is selected from 1, 3 and 4;
Q is either O (oxygen) or —O—C(O)—;
X is selected from a direct bond, —C($R_6$,$R_{14}$)—Y—, and —C($R_{13}$)=CH—;
Y is selected from a direct bond, O, S, and $C_1$–$C_4$alkylene;
$R_{13}$ is selected from hydrogen, $C_1$–$C_6$alkyl, $C_3$–$C_8$cycloalkyl, aryl, and benzyl;
$R_1$ and $R_2$ are independently selected from $C_3$–$C_8$alkoxyalkyl, $C_1$–$C_8$hydroxyalkyl, and $C_7$–$C_{12}$aralkyl; or
$R_1$ and $R_2$, are taken together with the nitrogen atom to which they are directly attached in formula (I), to form a ring denoted by formula (II):

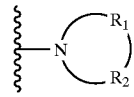

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$–$C_3$hydroxyalkyl, oxo, $C_2$–$C_4$acyl, $C_1$–$C_3$alkyl, $C_2$–$C_4$alkylcarboxy, $C_1$–$C_3$alkoxy, $C_1$–$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$–$C_8$carbocyclic ring, and any one or more of the additional nitrogen ring atoms may be substituted with substituents selected from hydrogen, $C_1$–$C_6$alkyl, $C_2$–$C_4$acyl, $C_2$–$C_4$hydroxyalkyl and $C_3$–$C_8$alkoxyalkyl; or $R_1$ and $R_2$, are taken together with the nitrogen atom to which they are directly attached in formula (I), to form a bicyclic ring system selected from 3-azabicyclo[3.2.2]nonan-3-yl, 2-aza-bicyclo[2.2.2]octan-2-yl, 3-azabicyclo[3.1.0]-hexan-3-yl, and 3-azabicyclo[3.2.0]-heptan-3-yl;

$R_3$ and $R_4$ are independently attached to the cycloalkyl ring shown in formula (I) at other than the 1 and 2 positions and are independently selected from hydrogen, hydroxy, $C_1$–$C_6$alkyl, and $C_1$–$C_6$alkoxy, and, when both $R_3$ and $R_4$ are attached to the same cycloalkane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$–$C_6$alkyl, aryl and benzyl, or $R_6$ and $R_{14}$, when taken together with the carbon to which they are attached, may form a spiro $C_3$–$C_5$cycloalkyl;

A is selected from $C_5$–$C_{12}$alkyl, a $C_3$–$C_{13}$carbocyclic ring, and ring systems selected from formulae (III), (IV), (V), (VI), (VII) and (VIII):

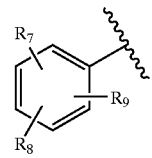

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2-C_7$alkanoyloxy, $C_1-C_6$alkyl, $C_1-C_6$alkoxy, $C_2-C_7$alkoxycarbonyl, $C_1-C_6$thioalkyl, aryl and $N(R_{15},R_{16})$ where $R_{15}$ and $R_{16}$ are independently selected from hydrogen, acetyl, methanesulfonyl, and $C_1-C_6$alkyl;

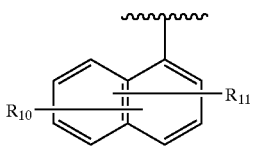

(IV)

and

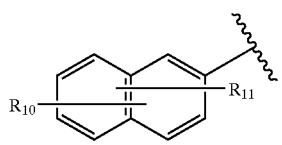

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2-C_7$alkanoyloxy, $C_1-C_6$alkyl, $C_1-C_6$alkoxy, $C_2-C_7$alkoxycarbonyl, $C_1-C_6$thioalkyl, and $N(R_{15},R_{16})$ where $R_{15}$ and $R_{16}$ are independently selected from hydrogen, acetyl, methanesulfonyl, and $C_1-C_6$alkyl;

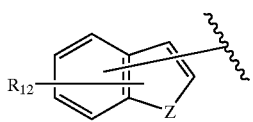

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2-C_7$alkanoyloxy, $C_1-C_6$alkyl, $C_1-C_6$alkoxy, $C_2-C_7$alkoxycarbonyl, $C_1-C_6$thioalkyl, and $N(R_{15},R_{16})$ where $R_{15}$ and $R_{16}$ are independently selected from hydrogen, acetyl, methanesulfonyl, and $C_1-C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1-C_6$alkyl, $C_3-C_8$cycloalkyl, aryl and benzyl;

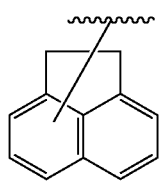

(VII)

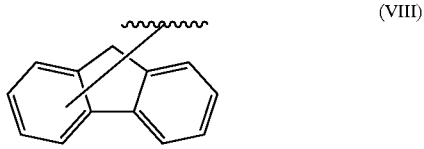

(VIII)

including isolated enantiomeric, diastereomeric and geometric isomers thereof, and mixtures thereof.

2. A composition comprising a compound selected from the group consisting of (1R,2R)-2-(4-Morpholinyl)-1-(2-naphthalenethoxy)cyclopentane; (1S,2S)-2-(4-Morpholinyl)-1-(2-naphthalenethoxy)cyclopentane; (1R,2R)-2-(3-Ketopyrrolidinyl)-1-(2,6-dichlorophenethoxy)cyclopentane; (1S, 2S)-2-(3-Ketopyrrolidinyl)-1-(2,6-dichlorophenethoxy)cyclopentane; and pharmaceutically acceptable salts and solvates of any of the foregoing; or a mixture of compounds selected from the group consisting of a mixture of (1R,2R)-2-(4-Morpholinyl)-1-(2-naphthalenethoxy)cyclopentane and (1S,2S)-2-(4-Morpholinyl)-1-(2-naphthalenethoxy)cyclopentane, a mixture of (1R,2R)-2-(3-Ketopyrrolidinyl)-1-(2,6-dichlorophenethoxy)cyclopentane and (1S, 2S)-2-(3-Ketopyrrolidinyl)-1-(2,6-dichlorophenethoxy)cyclopentane; and a mixture of pharmaceutically acceptable salts and solvates of any of the foregoing.

3. The composition of claim 1, wherein $R_1$ and $R_2$, are taken together with the nitrogen atom to which they are directly attached in formula (I), to form a ring denoted by formula (II):

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1-C_3$hydroxyalkyl, oxo, $C_2-C_4$acyl, $C_1-C_3$alkyl, $C_2-C_4$alkylcarboxy, $C_1-C_3$alkoxy, $C_1-C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3-C_8$carbocyclic ring, and any one or more of the additional nitrogen ring atoms may be substituted with substituents selected from hydrogen, $C_1-C_6$alkyl, $C_2-C_4$acyl, $C_2-C_4$hydroxyalkyl and $C_3-C_8$alkoxyalkyl; or $R_1$ and $R_2$, are taken together with the nitrogen atom to which they are directly attached in formula (I), to form a bicyclic ring system selected from 3-azabicyclo [3.2.2]nonan-3-yl, 2-aza-bicyclo[2.2.2]octan-2-yl, 3-azabicyclo[3.1.0]-hexan-3-yl, and 3-azabicyclo [3.2.0]-heptan-3-yl.

4. A method for treating arrhythmia in a warm-blooded animal comprising administering to a warm-blooded animal in need of such treatment a therapeutically effective amount of a composition according to claim 1 or 3 or a composition or mixture of compounds according to claim 2.

5. A method for modulating ion channel activity in a warm-blooded animal comprising administering to a warm-blooded animal in need of ion channel activity modulation a therapeutically effective amount of a composition according to claim 1 or 3 or a composition or mixture of compounds according to claim 2.

6. A method for modulating ion channel activity in vitro comprising contacting an in vitro ion channel with a composition according to claim 1 or 3 or a composition or mixture of compounds according to claim 2.

7. A pharmaceutical composition comprising an amount of a composition according to claim 1 or 3 or a composition or mixture of compounds according to claim 2 effective to treat diseases of the central nervous system in a warm-blooded animal in need of the treatment, and a pharmaceutically acceptable carrier, diluent, or excipient.

8. A method for treating diseases of the central nervous system in a warm-blooded animal comprising administering to a warm-blooded animal in need thereof a therapeutically effective amount of a composition according to claim 1 or 3 or a composition or mixture of compounds according to claim 2.

9. A pharmaceutical composition comprising an amount of a composition according to claim 1 or 3 or a composition or mixture of compounds according to claim 2 effective to treat convulsion in a warm-blooded animal in need of the treatment, and a pharmaceutically acceptable carrier, diluent, or excipient.

10. A method for treating convulsion in a warm-blooded animal comprising administering to a warm-blooded animal in need thereof a therapeutically effective amount of a composition according to claim 1 or 3 or a composition or mixture of compounds according to claim 2.

11. A pharmaceutical composition comprising an amount of a composition according to claim 1 or 3 or a composition or mixture of compounds according to claim 2 effective to treat epileptic spasms in a warm-blooded animal in need of the treatment, and a pharmaceutically acceptable carrier, diluent, or excipient.

12. A method for treating epileptic spasms in a warm-blooded animal comprising administering to a warm-blooded animal in need thereof a therapeutically effective amount of a composition according to claim 1 or 3 or a composition or mixture of compounds according to claim 2.

13. A pharmaceutical composition comprising an amount of a composition according to claim 1 or 3 or a composition or mixture of compounds according to claim 2 effective to treat depression, anxiety or schizophrenia, in a warm-blooded animal in need of the treatment, and a pharmaceutically acceptable carrier, diluent, or excipient.

14. A method for treating depression, anxiety or schizophrenia, in a warm-blooded animal comprising administering to a warm-blooded animal in need thereof a therapeutically effective amount of a composition according to claim 1 or 3 or a composition or mixture of compounds according to claim 2.

15. A pharmaceutical composition comprising an amount of a composition according to claim 1 or 3 or a composition or mixture of compounds according to claim 2 effective to treat Parkinson's disease in a warm-blooded animal in need of the treatment, and a pharmaceutically acceptable carrier, diluent, or excipient.

16. A method for treating Parkinson's disease in a warm-blooded animal comprising administering to a warm-blooded animal in need thereof a therapeutically effective amount of a composition according to claim 1 or 3 or a composition or mixture of compounds according to claim 2.

17. A pharmaceutical composition comprising an amount of a composition according to claim 1 or 3 or a composition or mixture of compounds according to claim 2 effective to treat respiratory disorders in a warm-blooded animal in need of the treatment, and a pharmaceutically acceptable carrier, diluent, or excipient.

18. A method for treating respiratory disorders in a warm-blooded animal comprising administering to a warm-blooded animal in need thereof a therapeutically effective amount of a composition according to claim 1 or 3 or a composition or mixture of compounds according to claim 2.

19. A pharmaceutical composition comprising an amount of a composition according to claim 1 or 3 or a composition or mixture of compounds according to claim 2 effective to treat cystic fibrosis in a warm-blooded animal in need of the treatment, and a pharmaceutically acceptable carrier, diluent, or excipient.

20. A method for treating cystic fibrosis in a warm-blooded animal comprising administering to a warm-blooded animal in need thereof a therapeutically effective amount of a composition according to claim 1 or 3 or a composition or mixture of compounds according to claim 2.

21. A pharmaceutical composition comprising an amount of a composition according to claim 1 or 3 or a composition or mixture of compounds according to claim 2 effective to treat asthma in a warm-blooded animal in need of the treatment, and a pharmaceutically acceptable carrier, diluent, or excipient.

22. A method for treating asthma in a warm-blooded animal comprising administering to a warm-blooded animal in need thereof a therapeutically effective amount of a composition according to claim 1 or 3 or a composition or mixture of compounds according to claim 2.

23. A pharmaceutical composition comprising an amount of a composition according to claim 1 or 3 or a composition or mixture of compounds according to claim 2 effective to treat a cough in a warm-blooded animal in need of the treatment, and a pharmaceutically acceptable carrier, diluent, or excipient.

24. A method for treating a cough in a warm-blooded animal comprising administration of a therapeutically effective amount of a composition according to claim 1 or 3 or a composition or mixture of compounds according to claim 2.

25. A pharmaceutical composition comprising an amount of a composition according to claim 1 or 3 or a composition or mixture of compounds according to claim 2 effective to treat inflammation in a warm-blooded animal in need of the treatment, and a pharmaceutically acceptable carrier, diluent, or excipient.

26. A method for treating inflammation in a warm-blooded animal comprising administering to a warm-blooded animal in need thereof a therapeutically effective amount of a composition according to claim 1 or 3 or a composition or mixture of compounds according to claim 2.

27. A pharmaceutical composition comprising an amount of a composition according to claim 1 or 3 or a composition or mixture of compounds according to claim 2 effective to treat arthritis in a warm-blooded animal in need of the treatment, and a pharmaceutically acceptable carrier, diluent, or excipient.

28. A method for treating arthritis in a warm-blooded animal comprising administering to a warm-blooded animal in need thereof a therapeutically effective amount of a composition according to claim 1 or 3 or a composition or mixture of compounds according to claim 2.

29. A pharmaceutical composition comprising an amount of a composition according to claim 1 or 3 or a composition or mixture of compounds according to claim 2 effective to treat allergies in a warm-blooded animal in need of the treatment, and a pharmaceutically acceptable carrier, diluent, or excipient.

30. A method for treating allergies in a warm-blooded animal comprising administering to a warm-blooded animal in need thereof a therapeutically effective amount of a composition according to claim 1 or 3 or a composition or mixture of compounds according to claim 2.

31. A pharmaceutical composition comprising an amount of a composition according to claim 1 or 3 or a composition or mixture of compounds according to claim 2 effective to treat gastrointestinal disorders in a warm-blooded animal in need of the treatment, and a pharmaceutically acceptable carrier, diluent, or excipient.

32. A method for treating gastrointestinal disorders in a warm-blooded animal comprising administering to a warm-blooded animal in need thereof a therapeutically effective amount of a compound according to claim 1 or a compound or mixture of compounds according to claim 2.

33. A pharmaceutical composition comprising an amount of a composition according to claim 1 or 3 or a composition or mixture of compounds according to claim 2 effective to treat urinary incontinence in a warm-blooded animal in need of the treatment, and a pharmaceutically acceptable carrier, diluent, or excipient.

34. A method for treating urinary incontinence in a warm-blooded animal comprising administering to a warm-blooded animal in need thereof a therapeutically effective amount of a composition according to claim 1 or 3 or a composition or mixture of compounds according to claim 2.

35. A pharmaceutical composition comprising an amount of a compound according to claim 1 or a compound or mixture of compounds according to claim 2 effective to treat irritable bowel syndrome in a warm-blooded animal in need of the treatment, and a pharmaceutically acceptable carrier, diluent, or excipient.

36. A method for treating irritable bowel syndrome in a warm-blooded animal comprising administering to a warm-blooded animal in need thereof a therapeutically effective amount of a composition according to claim 1 or 3 or a composition or mixture of compounds according to claim 2.

37. A pharmaceutical composition comprising an amount of a composition according to claim 1 or 3 or a composition or mixture of compounds according to claim 2 effective to treat cardiovascular diseases in a warm-blooded animal in need of the treatment, and a pharmaceutically acceptable carrier, diluent, or excipient.

38. A method for treating cardiovascular diseases in a warm-blooded animal comprising administering to a warm-blooded animal in need thereof a therapeutically effective amount of a composition according to claim 1 or 3 or a composition or mixture of compounds according to claim 2.

39. A pharmaceutical composition comprising an amount of a composition according to claim 1 or 3 or a composition or mixture of compounds according to claim 2 effective to treat cerebral or myocardial ischemias in a warm-blooded animal in need of the treatment, and a pharmaceutically acceptable carrier, diluent, or excipient.

40. A method for treating cerebral or myocardial ischemias in a warm-blooded animal comprising administering to a warm-blooded animal in need thereof a therapeutically effective amount of a composition according to claim 1 or 3 or a composition or mixture of compounds according to claim 2.

41. A pharmaceutical composition comprising an amount of a composition according to claim 1 or 3 or a composition or mixture of compounds according to claim 2 effective to treat hypertension in a warm-blooded animal in need of the treatment, and a pharmaceutically acceptable carrier, diluent, or excipient.

42. A method for treating hypertension in a warm-blooded animal comprising administering to a warm-blooded animal in need thereof a therapeutically effective amount of a composition according to claim 1 or 3 or a composition or mixture of compounds according to claim 2.

43. A pharmaceutical composition comprising an amount of a composition according to claim 1 or 3 or a composition or mixture of compounds according to claim 2 effective to treat long-QT syndrome in a warm-blooded animal in need of the treatment, and a pharmaceutically acceptable carrier, diluent, or excipient.

44. A method for treating long-QT syndrome in a warm-blooded animal comprising administering to a warm-blooded animal in need thereof a therapeutically effective amount of a composition according to claim 1 or 3 or a composition or mixture of compounds according to claim 2.

45. A pharmaceutical composition comprising an amount of a composition according to claim 1 or 3 or a composition or mixture of compounds according to claim 2 effective to treat stroke in a warm-blooded animal in need of the treatment, and a pharmaceutically acceptable carrier, diluent, or excipient.

46. A method for treating stroke in a warm-blooded animal comprising administering to a warm-blooded animal in need thereof a therapeutically effective amount of a composition according to claim 1 or 3 or a composition or mixture of compounds according to claim 2.

47. A pharmaceutical composition comprising an amount of a composition according to claim 1 or 3 or a composition or mixture of compounds according to claim 2 effective to treat migraine in a warm-blooded animal in need of the treatment, and a pharmaceutically acceptable carrier, diluent, or excipient.

48. A method for treating migraine in a warm-blooded animal comprising administering to a warm-blooded animal in need thereof a therapeutically effective amount of a composition according to claim 1 or 3 or a composition or mixture of compounds according to claim 2.

49. A pharmaceutical composition comprising an amount of a composition according to claim 1 or 3 or a composition or mixture of compounds according to claim 2 effective to treat ophthalmic diseases in a warm-blooded animal in need of the treatment, and a pharmaceutically acceptable carrier, diluent, or excipient.

50. A method for treating ophthalmic diseases in a warm-blooded animal comprising administering to a warm-blooded animal in need thereof a therapeutically effective amount of a composition according to claim 1 or 3 or a composition or mixture of compounds according to claim 2.

51. A pharmaceutical composition comprising an amount of a composition according to claim 1 or 3 or a composition or mixture of compounds according to claim 2 effective to treat diabetes mellitus in a warm-blooded animal in need of the treatment, and a pharmaceutically acceptable carrier, diluent, or excipient.

52. A method for treating diabetes mellitus in a warm-blooded animal comprising administering to a warm-blooded animal in need thereof a therapeutically effective amount of a composition according to claim 1 or 3 or a composition or mixture of compounds according to claim 2.

53. A pharmaceutical composition comprising an amount of a compound according to claim 1 or a compound or mixture of compounds according to claim 2 effective to treat myopathies in a warm-blooded animal in need of the treatment, and a pharmaceutically acceptable carrier, diluent, or excipient.

54. A method for treating myopathies in a warm-blooded animal comprising administering to a warm-blooded animal in need thereof a therapeutically effective amount of a compound according to claim 1 or a compound or mixture of compounds according to claim 2.

55. A pharmaceutical composition comprising an amount of a compound according to claim 1 or a compound or mixture of compounds according to claim 2 effective to treat Becker's myotonia in a warm-blooded animal in need of the treatment, and a pharmaceutically acceptable carrier, diluent, or excipient.

56. A method for treating Becker's myotonia in a warm-blooded animal comprising administering to a warm-blooded animal in need thereof a therapeutically effective amount of a compound according to claim 1 or a compound or mixture of compounds according to claim 2.

57. A pharmaceutical composition comprising an amount of a compound according to claim 1 or a compound or mixture of compounds according to claim 2 effective to treat myasthenia gravis in a warm-blooded animal in need of the treatment, and a pharmaceutically acceptable carrier, diluent, or excipient.

58. A method for treating myasthenia gravis in a warm-blooded animal comprising administering to a warm-blooded animal in need thereof a therapeutically effective amount of a compound according to claim 1 or a compound or mixture of compounds according to claim 2.

59. A pharmaceutical composition comprising an amount of a compound according to claim 1 or a compound or mixture of compounds according to claim 2 effective to treat paramyotonia congentia in a warm-blooded animal in need of the treatment, and a pharmaceutically acceptable carrier, diluent, or excipient.

60. A method for treating paramyotonia congentia in a warm-blooded animal comprising administering to a warm-blooded animal in need thereof a therapeutically effective amount of a compound according to claim 1 or a compound or mixture of compounds according to claim 2.

61. A pharmaceutical composition comprising an amount of a compound according to claim 1 or a compound or mixture of compounds according to claim 2 effective to treat malignant hyperthermia in a warm-blooded animal in need of the treatment, and a pharmaceutically acceptable carrier, diluent, or excipient.

62. A method for treating malignant hyperthermia in a warm-blooded animal comprising administering to a warm-blooded animal in need thereof a therapeutically effective amount of a compound according to claim 1 or a compound or mixture of compounds according to claim 2.

63. A pharmaceutical composition comprising an amount of a compound according to claim 1 or a compound or mixture of compounds according to claim 2 effective to treat hyperkalemic periodic paralysis in a warm-blooded animal in need of the treatment, and a pharmaceutically acceptable carrier, diluent, or excipient.

64. A method for treating hyperkalemic periodic paralysis in a warm-blooded animal comprising administering to a warm-blooded animal in need thereof a therapeutically effective amount of a compound according to claim 1 or a compound or mixture of compounds according to claim 2.

65. A pharmaceutical composition comprising an amount of a compound according to claim 1 or a compound or mixture of compounds according to claim 2 effective to treat Thomsen's myotonia in a warm-blooded animal in need of the treatment, and a pharmaceutically acceptable carrier, diluent, or excipient.

66. A method for treating Thomsen's myotonia in a warm-blooded animal comprising administering to a warm-blooded animal in need thereof a therapeutically effective amount of a compound according to claim 1 or a compound or mixture of compounds according to claim 2.

67. A pharmaceutical composition comprising an amount of a compound according to claim 1 or a compound or mixture of compounds according to claim 2 effective to treat autoimmune disorders in a warm-blooded animal in need of the treatment, and a pharmaceutically acceptable carrier, diluent, or excipient.

68. A method for treating autoimmune disorders in a warm-blooded animal comprising administering to a warm-blooded animal in need thereof a therapeutically effective amount of a compound according to claim 1 or a compound or mixture of compounds according to claim 2.

69. A pharmaceutical composition comprising an amount of a compound according to claim 1 or a compound or mixture of compounds according to claim 2 effective to treat graft rejection in organ transplantation or bone marrow transplantation in a warm-blooded animal in need of the treatment, and a pharmaceutically acceptable carrier, diluent, or excipient.

70. A method for treating graft rejection in organ transplantation or bone marrow transplantation in a warm-blooded animal comprising administering to a warm-blooded animal in need thereof a therapeutically effective amount of a compound according to claim 1 or a compound or mixture of compounds according to claim 2.

71. A pharmaceutical composition comprising an amount of a compound according to claim 1 or a compound or mixture of compounds according to claim 2 effective to produce local analgesia or anesthesia in a warm-blooded animal in need thereof, and a pharmaceutically acceptable carrier, diluent, or excipient.

72. A method for producing local analgesia or anesthesia in a warm-blooded animal in need thereof comprising administering to a warm-blooded animal in need thereof a therapeutically effective amount of a compound according to claim 1 or a compound or mixture of compounds according to claim 2.

73. A pharmaceutical composition comprising an amount of a compound according to claim 1 or a compound or mixture of compounds according to claim 2 effective to treat heart failure in a warm-blooded animal in need of the treatment, and a pharmaceutically acceptable carrier, diluent, or excipient.

74. A method for treating heart failure in a warm-blooded animal comprising administering to a warm-blooded animal in need thereof a therapeutically effective amount of a compound according to claim 1 or a compound or mixture of compounds according to claim 2.

75. A pharmaceutical composition comprising an amount of a compound according to claim 1 or a compound or mixture of compounds according to claim 2 effective to treat hypotension in a warm-blooded animal in need of the treatment, and a pharmaceutically acceptable carrier, diluent, or excipient.

76. A method for treating hypotension in a warm-blooded animal comprising administering to a warm-blooded animal in need thereof a therapeutically effective amount of a compound according to claim 1 or a compound or mixture of compounds according to claim 2.

77. A pharmaceutical composition comprising an amount of a compound according to claim 1 or a compound or mixture of compounds according to claim 2 effective to treat Alzheimer's disease in a warm-blooded animal in need of the treatment, and a pharmaceutically acceptable carrier, diluent, or excipient.

78. A method for treating Alzheimer's disease in a warm-blooded animal comprising administering to a warm-blooded animal in need thereof a therapeutically effective amount of a compound according to claim 1 or a compound or mixture of compounds according to claim 2.

79. A pharmaceutical composition comprising an amount of a compound according to claim 1 or a compound or mixture of compounds according to claim 2 effective to treat dementia in a warm-blooded animal in need of the treatment, and a pharmaceutically acceptable carrier, diluent, or excipient.

80. A method for treating dementia in a warm-blooded animal comprising administering to a warm-blooded animal in need thereof a therapeutically effective amount of a compound according to claim 1 or a compound or mixture of compounds according to claim 2.

81. A pharmaceutical composition comprising an amount of a compound according to claim 1 or a compound or mixture of compounds according to claim 2 effective to treat alopecia in a warm-blooded animal in need of the treatment, and a pharmaceutically acceptable carrier, diluent, or excipient.

82. A method for treating alopecia in a warm-blooded animal comprising administering to a warm-blooded animal in need thereof a therapeutically effective amount of a compound according to claim 1 or a compound or mixture of compounds according to claim 2.

83. A pharmaceutical composition comprising an amount of a compound according to claim 1 or a compound or mixture of compounds according to claim 2 effective to enhance libido in a warm-blooded animal in need thereof, and a pharmaceutically acceptable carrier, diluent, or excipient.

84. A method for enhancing libido in a warm-blooded animal in need thereof comprising administering to a warm-blooded animal in need thereof an enhancing amount of a compound according to claim 1 or a compound or mixture of compounds according to claim 2.

85. A composition according to claim 1 or 3 or a compound or mixture of compounds according to claim 2, and a pharmaceutically acceptable carrier, excipient or diluent.

86. The composition according to claim 1 wherein $R_1$ and $R_2$ are taken together with the nitrogen atom to which they are directly attached in formula (I) to form a ring denoted by formula (II):

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$–$C_3$hydroxyalkyl, oxo, $C_2$–$C_4$acyl, $C_1$–$C_3$alkyl, $C_2$–$C_4$alkylcarboxy, $C_1$–$C_3$alkoxy, and $C_1$–$C_{20}$alkanoyloxy.

87. The composition according to claim 86 wherein the ring of formula II is a substituted or unsubstituted morpholinyl group or a substituted or unsubstituted ketopyrrolidinyl group, wherein in the substituted groups any one or more of the carbon ring atoms in the ring may be substituted with one or two substituents selected from hydrogen, hydroxy, $C_1$–$C_3$hydroxyalkyl, oxo, $C_2$–$C_4$acyl, $C_1$–$C_3$alkyl, $C_2$–$C_4$alkylcarboxy, $C_1$–$C_3$alkoxy, and $C_1$–$C_{20}$alkanoyloxy.

88. The composition according to claim 86 wherein the ring of formula II is a saturated ring.

* * * * *